United States Patent
Komorowski et al.

(10) Patent No.: US 12,048,712 B2
(45) Date of Patent: Jul. 30, 2024

(54) BETA-ADRENERGIC AGONIST AND MUSCARINIC ANTAGONIST COMPOSITIONS AND METHODS OF USING

(71) Applicant: Bonafide Health, LLC, Harrison, NY (US)

(72) Inventors: James R. Komorowski, Trumbull, CT (US); Sarah Sylla, Brooklyn, NY (US); Devon Bernsley, New York, NY (US)

(73) Assignee: Bonafide Health, LLC, Harrison, NY (US)

( * ) Notice: Subject to any disclaimer, the term of this patent is extended or adjusted under 35 U.S.C. 154(b) by 0 days.

(21) Appl. No.: 18/381,558

(22) Filed: Oct. 18, 2023

(65) Prior Publication Data

US 2024/0122958 A1    Apr. 18, 2024

Related U.S. Application Data

(60) Provisional application No. 63/417,315, filed on Oct. 18, 2022.

(51) Int. Cl.

| | |
|---|---|
| *A61K 36/00* | (2006.01) |
| *A61K 31/235* | (2006.01) |
| *A61K 31/7076* | (2006.01) |
| *A61K 36/185* | (2006.01) |
| *A61K 36/31* | (2006.01) |
| *A61K 36/42* | (2006.01) |
| *A61K 36/54* | (2006.01) |
| *A61K 38/16* | (2006.01) |
| *A61P 13/06* | (2006.01) |

(52) U.S. Cl.
CPC ........ *A61K 31/7076* (2013.01); *A61K 31/235* (2013.01); *A61K 36/185* (2013.01); *A61K 36/31* (2013.01); *A61K 36/42* (2013.01); *A61K 36/54* (2013.01); *A61K 38/168* (2013.01); *A61P 13/06* (2018.01)

(58) Field of Classification Search
CPC .................................................. A61K 31/7076
See application file for complete search history.

(56) References Cited

U.S. PATENT DOCUMENTS

| 6,190,693 B1 | 2/2001 | Kafrissen et al. |
|---|---|---|
| 2009/0253705 A1 | 10/2009 | Berger et al. |
| 2012/0035118 A1 | 2/2012 | Caltabiano et al. |
| 2019/0151392 A1 | 5/2019 | Seipel |
| 2021/0213087 A1 | 7/2021 | Komorowski et al. |
| 2022/0202840 A1 | 6/2022 | Sigurdsson |
| 2023/0277581 A1 | 9/2023 | Komorowski |

FOREIGN PATENT DOCUMENTS

| CN | 103800219 A | 5/2014 | |
|---|---|---|---|
| CN | 109123032 | 1/2019 | |
| WO | WO-2012018773 A1 * | 2/2012 | ........ A61K 31/137 |
| WO | WO-2022/158504 | 7/2022 | |
| WO | WO 2023/168365 | 9/2023 | |
| WO | PCT/US2023/035433 | 10/2023 | |

OTHER PUBLICATIONS

Tallaride, Quantitative methods for assessing drug synergism, Genes & Cancer 2(11) 1003-1008, 2011 (Year: 2011).*
Raskin et al, Can an apple a day keep the doctor away, Current Pharmaceutical Designs, 2004, 10: 3419-3429 (Year: 2004).*
U.S. Appl. No. 18/381,087, filed Oct. 17, 2023, Komorowski.
Bottiglieri, "SAMe (S-Adenosyl-Methionine) Metabolic Function and Health Benefits," Medizioni, 2019: pp. 33-53.
Bright et al., "Developing and Validating the International Consultation on Incontinence Questionnaire Bladder Diary," European Urology, 2014: 66(2): pp. 294-300.
Brooks et al., "Beneficial effects of *Lepidium meyenii* (Maca) on psychological symptoms and measures of sexual dysfunction in postmenopausal women are not related to estrogen or androgen content," Menopause, 2008; 15(6): pp. 1157-1162.
Chapel Hill Gynecology, "Can you prevent early menopause", [online], [retrieved on May 15, 2023]. Retrieved from the Internet: <URL: https://chapelhillgynecology.com/can-you-prevent-early-menopause/, 2022, pp. 1-6.
Cleveland Clinic, "Overactive Bladder," [online], 2022, [retrieved on Oct. 24, 2023]. Retrieved from the Internet: <URL: https://my.clevelandclinic.org/health/diseases/14248-overactive-bladder>.
Cooper et al., "Active agents, biomaterials, and technologies to improve biolubrication and strengthen soft tissues," Biomaterials, 2018; 181: pp. 210-226.
Coyne et al., "The validation of the patient perception of bladder condition (PPBC): a single-item global measure for patients with overactive bladder," Eur Urol, 2006; 49(6): pp. 1079-1086.
Edwards et al., "Treating vulvovaginal atrophy/genitourinary syndrome of menopause: how important is vaginal lubricant and moisturizer composition?", Climacteric, 2016; 19(2): 151-161.
Erdem et al, "Management of overactive bladder and urge urinary incontinence in the elderly patient," Am J Med, 2006; 119(3 Suppl 1): pp. 29-36.
Gonzales, "Ethnobiology and Ethnopharmacology of *Lepidium meyenii* (Maca), a Plant from the Peruvian Highlands," Evidence-Based Complementary and Alternative Medicine, 2012; Article ID 193496, 10 pages.
Homma et al., "Symptom assessment tool for overactive bladder syndrome—overactive bladder symptom score," Urology, 2006; 68(2): pp. 318-323.

(Continued)

*Primary Examiner* — Qiuwen Mi
(74) *Attorney, Agent, or Firm* — Arnall Golden Gregory LLP

(57) ABSTRACT

Disclosed herein are compositions for supporting bladder health and/or treating, ameliorating, preventing, or reducing overactive bladder or the symptoms associated therewith. The compositions disclosed herein comprise a beta-adrenergic receptor agonist and at least one muscarinic receptor antagonist. Also described herein are methods utilizing the aforementioned compositions.

22 Claims, 12 Drawing Sheets

(56) References Cited

OTHER PUBLICATIONS

Hutchinson et al., "Overactive bladder syndrome: Management and treatment options," Aust J Gen Pract, 2020; 49(9): pp. 593-598.
International Search Report and Written Opinion issued in PCT/US2023/063620, mailed May 31, 2023.
Kadakia et al., "Phase II evaluation of S-adenosyl-L-methionine (SAMe) for the treatment of hot flashes," Support Care Cancer, 2016; 24(3): pp. 1061-1069.
Kumar et al., "Poly-γ-glutamic acid: A Promising Biopolymer," Defense Life Science Journal, 2018; 3(3): pp. 301-306.
Mansfield, "Muscarinic receptor antagonists, the overactive bladder and efficacy against urinary urgency," Clinical Medicine Insights: Therapeutics, 2010; 2: pp. 471-480.
Matza et al., "Test-retest reliability of four questionnaires for patients with overactive bladder: the overactive bladder questionnaire (OAB-q), patient perception of bladder condition (PPBC), urgency questionnaire (UQ), and the primary OAB symptom questionnaire (POSQ)," Neurourol Urodyn, 2005; 24(3): pp. 215-225.
Mayo Clinic, "Overactive Bladder", [online], 2022, [retrieved on Oct. 24, 2023]. Retrieved from the Internet: <URL: https://www.mayoclinic.org/diseases-conditions/overactive-bladder/symptoms-causes/syc-20355715>.
Mayo Clinic, "SAMe", [online], 2020, [retrieved on Oct. 24, 2023]. Retrieved from the Internet: <URL: https://www.mayoclinic.org/drugs-supplements-same/art-20364924>.
Meissner et al., "Hormone-Balancing Effect of Pre-Gelatinized Organic Maca (*Lepidium peruvianum* Chacon): (III) Clinical responses of early-postmenopausal women to Maca in double blind, randomized, Placebo-controlled, crossover configuration, outpatient study," Int J Biomed Sci, 2006; 2(4): pp. 375-394.
Ogunleye et al., "Poly-γ-glutamic acid: production, properties and applications," Microbiology, 2015; 161: pp. 1-17.
Rosano et al., "Menopause and cardiovascular disease: the evidence," Climacteric, 2007; 7(1). (abstract only).
Salmaggi et al., "Double-blind, placebo-controlled study of S-adenosyl-L-methionine in depressed postmenopausal women," Psychother Psychosom, 1993; 59(1): pp. 34-40.
Schoendorfer et al., "Urox containing concentrated extracts of *Crataeva nurvala* stem bark, *Equisetum arvense* stem and *Lindera aggregata* root, in the treatment of symptoms of overactive bladder and urinary incontinence: a phase 2, randomised, double-blind placebo controlled trial," BMC Complement Altern Med, 2018; 18(1): p. 42.
Symonds et al., "Development of a questionnaire on sexual quality of life in women," J Sex Marital Ther, 2005; 31(5): pp. 385-397.
U.S. Department of Health and Human Services, FDA, "Guidance for Industry: Q3C Impurities: Residual Solvents," Dec. 1997.
Yamanishi et al. "The role of M2-muscarinic receptors in mediating contraction of the pig urinary bladder in vitro", British Journal of Pharmacology, 2000; 131: pp. 1482-1488.
Yu et al., "Development of short forms from the PROMIS™ sleep disturbance and Sleep-Related Impairment item banks," Behav Sleep Med, 2011; 10(1): pp. 6-24.
Hedge, "Muscarinic receptors in the bladder: from basic research to therapeutics," British Journal of Pharmacology, 2006; 147(6): pp. S80-S87.
Berlanga et al., "Efficacy of S-Adenosyl-L-Methionine in Speeding the Onset of Action of imipramine," Psychiatry Res., 1992; 44(3): pp. 257-262.
Francioso et al., "Pharmacokinetic properties of a novel formulation of S-adenosyl-L-methionine phytate," Amino Acids, 2021; 53: pp. 1559-1568.
International Search Report and Written Opinion issued in PCT/US2023/035433, mailed Feb. 2, 2024.

* cited by examiner

Daily Diaries: Daytime Frequency

Daily Diaries: Nocturia

Daily Diaries: Daytime Urgency

Daily Diaries: Nighttime Urgency

Health-Related Quality of Life (HRQL) Score

Daytime Micturition Score

Nocturia Score

Urgency Score

BETA-ADRENERGIC AGONIST AND MUSCARINIC ANTAGONIST COMPOSITIONS AND METHODS OF USING

BACKGROUND

Adrenergic receptors are a class of G protein coupled receptors, whose corresponding biological agonists are catecholamines, such as norepinephrine and epinephrine. Compounds that agonistically bind to adrenergic receptors stimulate physiological responses associated with the sympathetic nervous system. Of the adrenergic receptors, the $\beta_2$ and $\beta_3$ adrenergic receptors have roles in bladder function, both of which, when activated by agonists, are responsible for the signaling cascade that causes relaxation of the detrusor smooth muscle of the bladder wall and increasing bladder capacity. Activation of the $\beta_2/\beta_3$ adrenergic receptors with agonists triggers this response via adenylate cyclase stimulation through Gs proteins, thereby increasing cyclic adenosine monophosphate (cAMP), and consequently mediating smooth muscle relaxation. In some instances, these signaling pathways can be affected by variations in the hormonal profile of an individual. For example, in some instances the hormonal profile of an individual changes because of menopause, and therefore menopause can affect the adrenergic receptor signaling pathways, and be responsible for symptoms of an irregular bladder, such as overactive bladder (OAB). Accordingly, researchers in this field have utilized knowledge of these $\beta$-adrenergic receptors and their signaling pathways to develop pharmaceutical agonist compounds to improve symptoms of abnormal bladder function such as OAB. Two such compounds are mirabegron (MYRBETRIQ®) and vibegron (GEMTESA®), both of which are FDA-approved drugs and are $\beta_3$-adrenergic receptor agonists. However, these compounds lead to a number of adverse side effects, such as hypertension, nasopharyngitis, urinary tract infections, headache, constipation, upper respiratory tract infection, arthralgia, diarrhea, tachycardia, abdominal pain, and fatigue.

Muscarinic acetylcholine receptors ("muscarinic receptors") are another class of G protein coupled receptors that are implicated in bladder function. Muscarinic receptors are activated by acetylcholine, and the binding of muscarinic receptors with acetylcholine, stimulates physiological responses associate with the parasympathetic nervous system. M1, M4, and M5 muscarinic receptors are prevalent in the central nervous system (CNS), and activation of these receptors is associated with mediating slow excitatory postsynaptic potentials and higher cognitive processes, such as learning and spatial memory (M1), and decreased locomotion (M4), whereas the clinical implications of the M5 muscarinic receptor are not well-understood. Of the remaining muscarinic receptors, the M2 and M3 muscarinic receptors have roles in bladder function when activated by acetylcholine. Activation of the M3 muscarinic receptor causes an upregulation of phospholipase C, and therefore, inositol triphosphate, which increases intracellular calcium, thereby mediating contraction of the detrusor smooth muscle of the bladder wall. Activation of the M2 muscarinic receptor causes a decrease in cAMP, and has been suggested to mediate contractile (re-contraction) responses to muscarinic agonists, i.e., acetylcholine, as evidenced by Yamanishi et al. "The role of M2-muscarinic receptors in mediating contraction of the pig urinary bladder in vitro". Therefore, activation of the M2 and M3 muscarinic receptors may result in OAB. Conversely, by providing antagonists, which block the activation of muscarinic receptors, the contraction of detrusor smooth muscle of the bladder wall can be reduced. Accordingly, researchers in this field have utilized knowledge of these muscarinic receptors and their signaling pathways to develop antagonist compounds to improve symptoms of an irregular bladder, such as OAB. Tolterodine (Detrol®), oxybutynin (DITROPAN®), trospium (SANCTURA®), darifenacin (ENABLEX®), solifenacin (VESIcare®), and fesoterodine (TOVIAZ™), are FDA-approved drugs and are muscarinic antagonists. These drugs can result in improvements after about 12 weeks, but they are well-known to lead to high incident rates of adverse side effects such as dry mouth, constipation, heartburn, blurry vision, rapid heartbeat (tachycardia), flushed skin, urinary retention, and cognitive side effects, such as impaired memory, brain fog, and confusion. These adverse side effects occur due to a lack of binding selectivity of antimuscarinic agents for M2/M3 muscarinic receptors over M1/M4 muscarinic receptors and often result in the duration for administration of these muscarinic agonists to subjects being less than 1 year, thereby reducing their overall long-term effectiveness or a subject's willingness for repeat or ongoing usage.

In light of these findings, the inventors have identified a growing demand to develop beta-adrenergic receptor agonists and muscarinic receptor antagonists with reduced incidence of undesirable effects. The inventors have noted the relationship between the beta-adrenergic and muscarinic receptors, the role their associated signaling pathways play in bladder health, normal bladder function, and in conditions, disorders, or diseases of the bladder, such as OAB, and that beta-adrenergic receptor agonists and muscarinic receptor antagonists can alleviate, ameliorate, treat, or cure such. Beta-adrenergic receptor agonists and muscarinic receptor antagonists are believed to confer many potential benefits to subjects to support bladder health and maintain normal bladder function, and the inventors have discovered the use of beta-adrenergic receptor agonists and muscarinic receptor antagonists in combination provide superior, and unexpected benefits, compared to the individual agonists/antagonists alone. This finding is novel. As such, by providing beta-adrenergic receptor agonists and muscarinic receptor antagonists together as pharmaceutical agents and/or dietary supplements, therapeutic and nutraceutical benefits can be realized, either individually, collectively, or in conjunction with other pharmaceutical agents and/or dietary supplements.

SUMMARY

Embodiments of the present disclosure relate to novel beta-adrenergic receptor agonists, muscarinic receptor antagonists and their use for bladder health and in the amelioration and/or treatment of OAB or symptoms associated therewith.

These and other features, aspects, and advantages of the present embodiments will become understood with reference to the following description, appended claims, and accompanying figures.

DETAILED DESCRIPTION

Figure 1:
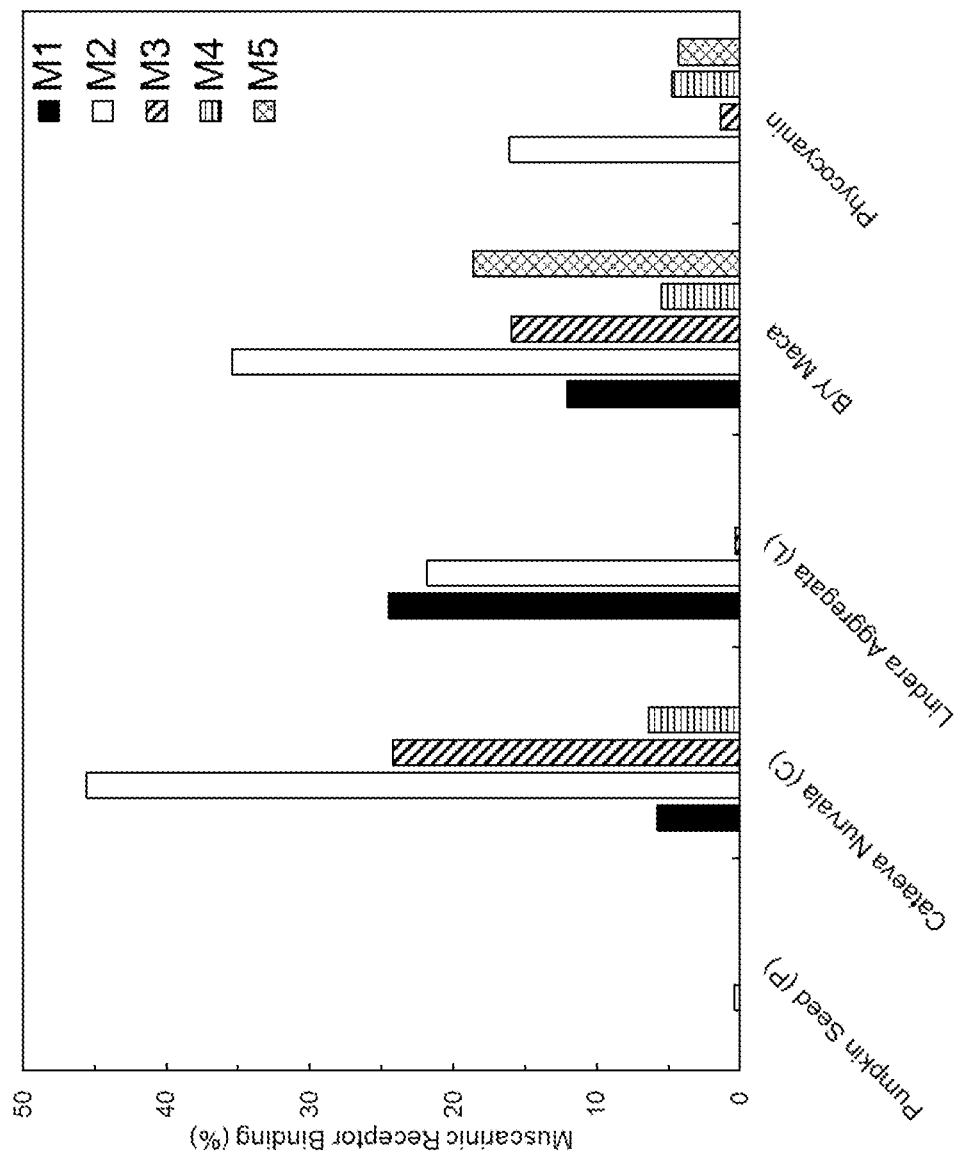
FIG. 1 shows the maximum binding percentage for the muscarinic receptors: M1 (solid fill), M2 (empty fill), M3 (diagonal fill), M4 (horizontal fill), and M5 (cross-hatch fill) of a pumpkin seed composition (P), a *Crataeva nurvala* composition (C), a *Lindera aggregata* composition (L), a 1:1 mixture of black (B) and yellow (Y) maca, and a phycocyanin composition, according to one or more embodiments of the disclosure, for a dose range of 0.05-1000 µg evaluated in vitro.

Some embodiments provide a composition comprising an amount of pumpkin seed formulated as a pumpkin seed composition. Certain pumpkin seed compositions comprise a pharmaceutically acceptable vehicle, carrier, or diluent. In certain embodiments, a pumpkin seed composition can comprise ground pumpkin seed, an extract of pumpkin seed, or a combination thereof. Some embodiments can be formulated to have varying amounts of these constituents.

Certain embodiments provide a composition comprising an amount of *Crataeva nurvala* formulated as a *Crataeva nurvala* composition. Certain *Crataeva nurvala* compositions comprise a pharmaceutically acceptable vehicle, carrier, or diluent. In certain embodiments, a *Crataeva nurvala* composition can comprise ground *Crataeva nurvala* plant material, an extract of *Crataeva nurvala* plant material, or a combination thereof. Some embodiments can be formulated to have varying amounts of these constituents. As used herein, the term "*Crataeva nurvala* plant material" may refer to roots, stems, bark, leaves, flowers, fruits, and/or seeds of the *Crataeva nurvala* plant; the term "ground *Crataeva nurvala* plant material" may refer to small particles or powder of dried roots, stems, bark, leaves, flowers, fruits, and/or seeds of the *Crataeva nurvala* plant; and the term "an extract of *Crataeva nurvala* plant material" may refer to a substance extracted from roots, stems, bark, leaves, flowers, fruits, and/or seeds of the *Crataeva nurvala* plant material using extraction solvents.

Certain embodiments provide a composition comprising an amount of *Lindera aggregata* formulated as a *Lindera aggregata* composition. Certain *Lindera aggregata* compositions comprise a pharmaceutically acceptable vehicle, carrier, or diluent. In certain embodiments, a *Lindera aggregata* composition can comprise ground *Lindera aggregata* plant material, an extract of *Lindera aggregata* plant material, or the combination thereof. Some embodiments can be formulated to have varying amounts of these constituents. As used herein, the term "*Lindera aggregata* plant material" can refer to roots, stems, bark, leaves, flowers, fruits, and/or seeds of the *Lindera aggregata* plant; the term "ground *Lindera aggregata* plant material" may refer to small particles or powder of dried roots, stems, bark, leaves, flowers, fruits, and/or seeds of the *Lindera aggregata* plant; and the term "an extract of *Lindera aggregata* plant material" may refer to a substance extracted from roots, stems, bark, leaves, flowers, fruits, and/or seeds of the *Lindera aggregata* plant material using extraction solvents.

Certain embodiments provide a composition comprising an amount of black and/or an amount of yellow *Lepidium meyenii* (maca) formulated as a black and/or yellow maca composition. Certain black and/or yellow maca compositions comprise a pharmaceutically acceptable vehicle, carrier, or diluent. Certain embodiments may comprise ground black maca, ground yellow maca, a mixture of both ground black maca and ground yellow maca, extracts thereof, or any combination thereof. Some embodiments can be formulated to have varying amounts of these constituents. Embodiments formulated as a mixture of both black and yellow maca composition may comprise a ratio of black to yellow maca of about 1:1, or a black to yellow ratio of about 4:1 to about 1:4, and ranges therebetween.

Certain embodiments provide a composition comprising an amount of phycocyanin formulated as a phycocyanin composition. Certain phycocyanin compositions comprise a pharmaceutically acceptable vehicle, carrier, or diluent. Certain embodiments may comprise phycocyanin, an extract of phycocyanin, or the combination thereof. Some embodiments can be formulated to have varying amounts of these constituents.

Some embodiments provide a composition comprising an amount of s-adenosyl-L-methionine (SAMe) formulated as a SAMe composition. Certain SAMe compositions comprise a pharmaceutically acceptable vehicle, carrier, or diluent. Some embodiments can be formulated to have varying amounts of these constituents. In some embodiments, a SAMe composition, as described herein, can be further provided with a compound that improves its absorption. In certain embodiments the absorption-improving compound is propyl gallate (PG). Some embodiments provide a composition comprising an amount of SAMe and an amount PG formulated as a SAMe and PG composition. Certain SAMe and PG compositions comprise a pharmaceutically acceptable vehicle, carrier, or diluent. Some embodiments can be formulated to have varying amounts of these constituents. Certain embodiments may be formulated as a composition that comprises a SAMe to PG ratio of about 32:1, or a SAMe to PG ratio of about 128:1 to about 8:1, and ranges therebetween.

As set forth herein, the compositions of some embodiments may comprise at least one of a pumpkin seed composition, a *Crataeva nurvala* composition, a *Lindera aggregata* composition, a black and/or yellow maca composition, a phycocyanin composition, a SAMe composition, and a SAMe and PG composition.

In certain embodiments, the composition may comprise a combination of a pumpkin seed composition, a *Crataeva nurvala* composition, a *Lindera aggregata* composition. The particular ratio of the pumpkin seed composition, the *Crataeva nurvala* composition, and the *Lindera aggregata* composition (P+C+L) are not particularly limited. In some embodiments, the aforementioned components can be present in a ratio of about 1:1:1, 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1, 2:1:2, 2:1:3, 2:1:4, 2:1:5, 2:1:6, 2:1:7, 2:1:8, 2:1:9, 2:1:10, 2:2:1, 2:2:2, 2:2:3, 2:2:4, 2:2:5, 2:2:6, 2:2:7, 2:2:8, 2:2:9, 2:2:10, 2:3:1, 2:3:2, 2:3:3, 2:3:4, 2:3:5, 2:3:6, 2:3:7, 2:3:8, 2:3:9, 2:3:10, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1, 3:1:2, 3:1:3, 3:1:4, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1, 4:1:2, 4:1:3, 4:1:4, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1, 5:1:2, 5:1:3, 5:1:4, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, 10:10:10, or any ratio in between. In view of the results and discussion contained herein, one of skill in the art would understand how to formulate a P+C+L composition of the instant disclosure to achieve the results described herein.

In certain embodiments, the composition may comprise a combination of a pumpkin seed composition, a *Crataeva nurvala* composition, a *Lindera aggregata* composition (P+C+L) and at least one of a black and/or yellow maca composition, a phycocyanin composition, a SAMe composition, or a SAMe and PG composition. The particular ratio of the P+C+L composition to the at least one other component is not particularly limited. In some embodiments, the ratio of P+C+L to the at least one other component can be present in a ratio of about 1:0.1, 1:0.2, 1:0.3, 1:0.4, 1:0.5, 1:0.6, 1:0.7, 1:0.8, 1:0.9, 1:1, 2:1, 3:1, 4:1, 5:1, 6:1 7:1, 8:1, 9:1, 10:1, 1:2, 1:3, 1:4, 1:5, 1:6, 1:7, 1:8, 1:9, 1:10, or any ratio in between. In view of the results and discussion contained herein, one of skill in the art would understand how to formulate a composition comprising a composition of P+C+L and at least one of a black and/or yellow maca composition, a phycocyanin composition, a SAMe composition, or a SAMe and PG composition of the instant disclosure to achieve the results described herein.

In certain embodiments, the composition may comprise a combination of a *Crataeva nurvala* composition and at least one of a black and/or yellow maca composition, a phycocyanin composition, a SAMe composition, or a SAMe and PG composition. The particular ratio of the *Crataeva nurvala* composition to the at least one other component is not particularly limited. In some embodiments, the ratio of the *Crataeva nurvala* composition to the at least one other component can be present in a ratio of about 1:1, 2:1, 3:1, 4:1, 5:1, 6:17:1, 8:1, 9:1, 10:1, 1:2, 1:3, 1:4, 1:5, 1:6, 1:7, 1:8, 1:9, 1:10, or any ratio in between. In view of the results and discussion contained herein, one of skill in the art would understand how to formulate a composition comprising a composition of *Crataeva nurvala* composition and at least one of a black and/or yellow maca composition, a phycocyanin composition, a SAMe composition, or a SAMe and PG composition of the instant disclosure to achieve the results described herein.

In certain embodiments, the composition may comprise a combination of a *Crataeva nurvala* composition, a black and/or yellow maca composition, and a SAMe composition. The particular ratio of the *Crataeva nurvala* composition to the black and/or yellow maca composition and the SAMe composition is not particularly limited. In some embodiments, the ratio of the *Crataeva nurvala* composition to the black and/or yellow maca composition and the SAMe composition can be present in a ratio of about 1:1:1.0, 1:1:1.1, 1:1:1.2, 1:1:1.3, 1:1:1.4, 1:1:1.5, 1:1:1.6, 1:1:1.7, 1:1:1.8, 1:1:1.9, 1:1:2.0, 1:1:2.1, 1:1:2.2, 1:1:2.3, 1:1:2.4, 1:1:2.5, 1:1:2.6, 1:1:2.7, 1:1:2.8, 1:1:2.9, 1:1:3.0, 1:1:3.1, 1:1:3.2, 1:1:3.3, 1:1:3.4, 1:1:3.5, 1:1:3.6, 1:1:3.7, 1:1:3.8, 1:1:3.9, 1:1:4.0, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1.0, 2:1:1.1, 2:1:1.2, 2:1:1.3, 2:1:1.4, 2:1:1.5, 2:1:1.6, 2:1:1.7, 2:1:1.8, 2:1:1.9, 2:1:2.0, 2:1:2.1, 2:1:2.2, 2:1:2.3, 2:1:2.4, 2:1:2.5, 2:1:2.6, 2:1:2.7, 2:1:2.8, 2:1:2.9, 2:1:3.0, 2:1:3.1, 2:1:3.2, 2:1:3.3, 2:1:3.4, 2:1:3.5, 2:1:3.6, 2:1:3.7, 2:1:3.8, 2:1:3.9, 2:1:4.0, 2:1:5, 2:1:6, 2:1:7, 2:1:8, 2:1:9, 2:1:10, 2:2:1.0, 2:2:1.1, 2:2:1.2, 2:2:1.3, 2:2:1.4, 2:2:1.5, 2:2:1.6, 2:2:1.7, 2:2:1.8, 2:2:1.9, 2:2:3, 2:2:4, 2:2:5, 2:2:6, 2:2:7, 2:2:8, 2:2:9, 2:2:10, 2:3:1.0, 2:3:1.1, 2:3:1.2, 2:3:1.3, 2:3:1.4, 2:3:1.5, 2:3:1.6, 2:3:1.7, 2:3:1.8, 2:3:1.9, 2:3:2.0, 2:3:3, 2:3:4, 2:3:5, 2:3:6, 2:3:7, 2:3:8, 2:3:9, 2:3:10, 2:3:1:1.0, 2:3.1:1.1, 2:3.1:1.2, 2:3.1:1.25, 2:3.125:1.25, 2:3.1:1.3, 2:3.1:1.4, 2:3.1:1.5, 2:3.1:1.6, 2:3.1:1.7, 2:3.1:1.8, 2:3.1:1.9, 2:3.1:2.0, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1.0, 3:1:1.1, 3:1:1.2, 3:1:1.3, 3:1:1.4, 3:1:1.5, 3:1:1.6, 3:1:1.7, 3:1:1.8, 3:1:1.9, 3:1:2.0, 3:1:2.1, 3:1:2.2, 3:1:2.3, 3:1:2.4, 3:1:2.5, 3:1:2.6, 3:1:2.7, 3:1:2.8, 3:1:2.9, 3:1:3.0, 3:1:3.1, 3:1:3.2, 3:1:3.3, 3:1:3.4, 3:1:3.5, 3:1:3.6, 3:1:3.7, 3:1:3.8, 3:1:3.9, 3:1:4.0, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1.0, 4:1:1.1, 4:1:1.2, 4:1:1.3, 4:1:1.4, 4:1:1.5, 4:1:1.6, 4:1:1.7, 4:1:1.8, 4:1:1.9, 4:1:2.0, 4:1:2.1, 4:1:2.2, 4:1:2.3, 4:1:2.4, 4:1:2.5, 4:1:2.6, 4:1:2.7, 4:1:2.8, 4:1:2.9, 4:1:3.0, 4:1:3.1, 4:1:3.2, 4:1:3.3, 4:1:3.4, 4:1:3.5, 4:1:3.6, 4:1:3.7, 4:1:3.8, 4:1:3.9, 4:1:4.0, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1.0, 5:1:1.1, 5:1:1.2, 5:1:1.3, 5:1:1.4, 5:1:1.5, 5:1:1.6, 5:1:1.7, 5:1:1.8, 5:1:1.9, 5:1:2.0, 5:1:2.1, 5:1:2.2, 5:1:2.3, 5:1:2.4, 5:1:2.5, 5:1:2.6, 5:1:2.7, 5:1:2.8, 5:1:2.9, 5:1:3.0, 5:1:3.1, 5:1:3.2, 5:1:3.3, 5:1:3.4, 5:1:3.5, 5:1:3.6, 5:1:3.7, 5:1:3.8, 5:1:3.9, 5:1:4.0, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, 10:10:10 or any ratio in between. The amount of the *Crataeva nurvala* composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 360 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of the black maca and/or yellow maca composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of the SAMe composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. In certain embodiments, the composition may comprise a combination of 100-500 mg of a *Crataeva nurvala* composition, 40-1000 mg of a black and/or yellow maca composition, and 100-500 mg of a SAMe composition. In certain embodiments, the composition may comprise a combination of 300-400 mg of a *Crataeva nurvala* composition, 90-500 mg of a black and/or yellow maca composition, and 150-200 mg of a SAMe composition. In view of the results and discussion contained herein, one of skill in the art would understand how to formulate a composition comprising a composition of *Crataeva nurvala* composition, a black and/or yellow maca composition, and a SAMe composition of the instant disclosure to achieve the results described herein.

In certain embodiments, the composition may comprise a combination of a *Crataeva nurvala* composition, a black and/or yellow maca composition, and a SAMe and PG composition. The particular ratio of the *Crataeva nurvala* composition to the black and/or yellow maca composition and the SAMe and PG composition is not particularly limited. In some embodiments, the ratio of the *Crataeva nurvala* composition to the black and/or yellow maca composition and the SAMe and PG composition can be present in a ratio of about 1:1:1.0, 1:1:1.1, 1:1:1.2, 1:1:1.3, 1:1:1.4, 1:1:1.5, 1:1:1.6, 1:1:1.7, 1:1:1.8, 1:1:1.9, 1:1:2.0, 1:1:2.1, 1:1:2.2, 1:1:2.3, 1:1:2.4, 1:1:2.5, 1:1:2.6, 1:1:2.7, 1:1:2.8, 1:1:2.9, 1:1:3.0, 1:1:3.1, 1:1:3.2, 1:1:3.3, 1:1:3.4, 1:1:3.5, 1:1:3.6, 1:1:3.7, 1:1:3.8, 1:1:3.9, 1:1:4.0, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1.0, 2:1:1.1, 2:1:1.2, 2:1:1.3, 2:1:1.4, 2:1:1.5, 2:1:1.6, 2:1:1.7, 2:1:1.8, 2:1:1.9, 2:1:2.0, 2:1:2.1, 2:1:2.2, 2:1:2.3, 2:1:2.4, 2:1:2.5, 2:1:2.6, 2:1:2.7, 2:1:2.8, 2:1:2.9, 2:1:3.0, 2:1:3.1, 2:1:3.2, 2:1:3.3, 2:1:3.4, 2:1:3.5, 2:1:3.6, 2:1:3.7, 2:1:3.8, 2:1:3.9, 2:1:4.0, 2:1:5, 2:1:6, 2:1:7, 2:1:8, 2:1:9, 2:1:10, 2:2:1.0, 2:2:1.1, 2:2:1.2, 2:2:1.3, 2:2:1.4, 2:2:1.5, 2:2:1.6, 2:2:1.7, 2:2:1.8, 2:2:1.9, 2:2:3, 2:2:4, 2:2:5, 2:2:6, 2:2:7, 2:2:8, 2:2:9, 2:2:10, 2:3:1.0, 2:3:1.1, 2:3:1.2, 2:3:1.3, 2:3:1.4, 2:3:1.5, 2:3:1.6, 2:3:1.7, 2:3:1.8, 2:3:1.9, 2:3:2.0, 2:3:3, 2:3:4, 2:3:5, 2:3:6, 2:3:7, 2:3:8, 2:3:9, 2:3:10, 2:3.1:1.0, 2:3.1:1.1, 2:3.1:1.2, 2:3.1:1.25, 2:3.125:1.25, 2:3.1:1.3, 2:3.1:1.4, 2:3.1:1.5, 2:3.1:1.6, 2:3.1:1.7, 2:3.1:1.8, 2:3.1:1.9, 2:3.1:2.0, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1.0, 3:1:1.1, 3:1:1.2, 3:1:1.3, 3:1:1.4, 3:1:1.5, 3:1:1.6, 3:1:1.7, 3:1:1.8, 3:1:1.9, 3:1:2.0, 3:1:2.1, 3:1:2.2, 3:1:2.3, 3:1:2.4, 3:1:2.5, 3:1:2.6, 3:1:2.7, 3:1:2.8, 3:1:2.9, 3:1:3.0, 3:1:3.1, 3:1:3.2, 3:1:3.3, 3:1:3.4, 3:1:3.5, 3:1:3.6, 3:1:3.7, 3:1:3.8, 3:1:3.9, 3:1:4.0, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1.0, 4:1:1.1, 4:1:1.2, 4:1:1.3, 4:1:1.4, 4:1:1.5, 4:1:1.6, 4:1:1.7, 4:1:1.8, 4:1:1.9, 4:1:2.0, 4:1:2.1, 4:1:2.2, 4:1:2.3, 4:1:2.4, 4:1:2.5, 4:1:2.6, 4:1:2.7, 4:1:2.8, 4:1:2.9, 4:1:3.0, 4:1:3.1, 4:1:3.2, 4:1:3.3, 4:1:3.4, 4:1:3.5, 4:1:3.6, 4:1:3.7, 4:1:3.8, 4:1:3.9, 4:1:4.0, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1.0, 5:1:1.1, 5:1:1.2, 5:1:1.3, 5:1:1.4, 5:1:1.5, 5:1:1.6, 5:1:1.7, 5:1:1.8, 5:1:1.9, 5:1:2.0, 5:1:2.1, 5:1:2.2, 5:1:2.3, 5:1:2.4, 5:1:2.5, 5:1:2.6, 5:1:2.7, 5:1:2.8, 5:1:2.9, 5:1:3.0, 5:1:3.1, 5:1:3.2, 5:1:3.3, 5:1:3.4, 5:1:3.5, 5:1:3.6, 5:1:3.7, 5:1:3.8, 5:1:3.9, 5:1:4.0, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, 10:10:10 or any ratio in between. The amount of the *Crataeva nurvala* composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 360 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of the black maca and/or yellow maca composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of the SAMe and PG composition in the combination may be about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. In certain embodiment, the composition may comprise a combination of 100-500 mg of a *Crataeva nurvala* composition, 40-1000 mg of a black and/or yellow maca composition, and 100-500 mg of a SAMe and PG composition. In certain embodiment, the composition may comprise a combination of 300-400 mg of a *Crataeva nurvala* composition, 90-500 mg of a black and/or yellow maca composition, and 150-200 mg of a SAMe and PG composition. In view of the results and discussion contained herein, one of skill in the art would understand how to formulate a composition comprising a composition of *Crataeva nurvala* composition, a black and/or yellow maca composition, and a SAMe and PG composition of the instant disclosure to achieve the results described herein.

Compositions, as disclosed herein, can be formulated as a dietary supplement or pharmaceutical agent. A composition of the instant disclosure can further comprise a matrix material such as a fatty acid, fatty acid ester, triglycerides, oils, lipid solvents, and the like. In some embodiments, a composition is a solid composition. In some embodiments, the composition comprises a sustained-release matrix. In some embodiments, the composition is enteric coated.

In certain embodiments, a composition may comprise an amount of a beta-adrenergic receptor agonist and an amount of a muscarinic receptor antagonist. In some embodiments the beta-adrenergic receptor agonist comprises an amount of a SAMe composition, as described herein. The SAMe composition can be further provided with a compound that improves its absorption, such as PG. In some embodiments the muscarinic receptor antagonist is selected from the group consisting of a pumpkin seed composition, as described herein, a *Crataeva nurvala* composition, as described herein, a *Lindera aggregata* composition, as described herein, a black and/or yellow maca composition, as described herein, a phycocyanin composition, as described herein, and any combination thereof. In some embodiments the muscarinic receptor antagonist is selected from the group a *Crataeva nurvala* composition, as described herein, a black and/or yellow maca composition, as described herein, and any combination thereof. In certain embodiments, a composition as described herein is administered to a subject to support bladder health. In certain embodiments, a composition as described herein is administered to a subject to maintain normal bladder function. In certain embodiments, a composition as described herein is administered to a subject to maintain healthy levels of bladder activity and urinary frequency. In certain embodiments, a composition as described herein is administered to a subject to maintain healthy levels of bladder activity and urinary frequency. In certain embodiments, a composition as described herein is administered to a subject to maintain healthy levels of one or more of urinary urgency, urinary incontinence, urge incontinence, polyuria, nocturia, bladder spasms, and any combination thereof. In certain embodiments, a composition as described herein is administered to a subject to treat, ameliorate, prevent, or reduce the effects of overactive bladder or at least one symptom associated therewith, wherein the at least one symptom is selected from the group consisting of urinary urgency, urinary incontinence, urge incontinence, polyuria, nocturia, bladder spasms, and any combination thereof.

Without being bound by a particular theory, it is believed that the compositions, dietary supplements, and/or pharmaceutical agents disclosed herein act as either beta-adrenergic receptor agonists or muscarinic receptor antagonists and target signaling pathways associated with bladder health and normal bladder function. It is believed that symptoms of abnormal bladder function, such as overactive bladder or the symptoms associated therewith, is caused, in part, by frequent and unexpected contraction of the detrusor smooth muscle in the bladder. In the case of the beta-adrenergic receptor, it is believed that overactive bladder or the symptoms thereof are characterized and result from an insufficient activation of $\beta_2$ and $\beta_3$ adrenergic receptors. When the $\beta_2$- and $\beta_3$-adrenergic receptors are activated, the associated Gs proteins are stimulated triggering a response of adenylate cyclase resulting in the increased production of cAMP, which mediates relaxation of the detrusor smooth muscle in the bladder. Therefore, by providing beta-adrenergic receptor agonists, which activate this pathway, undesired and unexpected contractions of the detrusor smooth muscle in the bladder can be minimized and/or prevented, and therefore OAB and its associated symptoms, can be treated, ameliorated, prevented, or reduced and normal bladder function can be maintained or restored. In the case of the muscarinic receptor, it is believed that overactive bladder or the symptoms thereof are characterized and result from activation of the M2 and M3 muscarinic receptors by acetylcholine. When the M2 muscarinic receptor is activated by acetylcholine, the amount of cAMP production decreases, and this reduced amount of cAMP reduces the relaxation of the detrusor smooth muscle in the bladder. Activation of the M3 muscarinic receptor, on the other hand, causes an upregulation of phospholipase C, and therefore, inositol triphosphate, which increases intracellular calcium, thereby mediating contraction of the detrusor smooth muscle of the bladder wall. Moreover, activation of the M1 and M4 muscarinic receptors are associated with mediating slow excitatory postsynaptic potentials and higher cognitive processes, such as learning and spatial memory (M1), and decreased locomotion (M4). It is believed that blocking activation of the M1 and M4 muscarinic receptors may be the cause of the negative side-effects associated with muscarinic antagonists of the field, e.g., dry mouth, constipation, heartburn, blurry vision, rapid heartbeat (tachycardia), flushed skin, urinary retention, and cognitive side effects, such as impaired memory, brain fog, and confusion. By providing compounds that specifically target the M2 and M3 muscarinic receptors, it is believed that OAB and its associated symptoms can be treated, ameliorated, prevented, or reduced and normal bladder function can be maintained or restored while also minimizing or reducing the incidence of undesired side effects/adverse events associated with antagonistic interaction with the M1 and M4 muscarinic receptors, e.g. dry mouth, constipation, heartburn, blurry vision, rapid heartbeat (tachycardia), flushed skin, urinary retention, and cognitive side effects, such as impaired memory, brain fog, and confusion. It is also believed that the compositions disclosed herein and the methods described herein can be implemented to support bladder health and maintain healthy bladder behavior, including avoiding or reducing the severity of outcomes associated with OAB, including antagonistic interaction with the M1 and M4 muscarinic receptors, e.g. dry mouth, constipation, heartburn, blurry vision, rapid heartbeat (tachycardia), flushed skin, urinary retention, and cognitive side effects, such as impaired memory, brain fog, and confusion.

The known compounds in this field do not preferentially bind the M2 and M3 muscarinic receptors relative to the M1 and M4 muscarinic receptors, unlike the compositions described herein. Accordingly, the known compounds in this field have a significant prevalence of undesired effects/adverse events, as described herein, and as would be recognized by the skilled artisan when viewing the disclosure contained herein. The embodiments disclosed herein demonstrate unexpected and superior results by selectively binding the M2 and M3 muscarinic receptors, relative to the M1 and M4 muscarinic receptors. Therefore, the embodiments disclosed herein can treat, ameliorate, prevent, or reduce OAB or its associated symptoms and thus maintain and/or restore normal bladder function while minimizing or reducing the incidence of undesired side effects/adverse events, or are otherwise utilized to maintain healthy levels of bladder function as it relates to OAB.

In some embodiments, a composition as described herein can comprise one or more supplement ingredients. As used herein, the term supplement ingredient can refer to essential fatty acids such as linolenic acid and linoleic acid, and essential amino acids such as tryptophan, lysine, methionine, phenylalanine, threonine, valine, leucine, isoleucine, arginine, and histidine, n-acetyl cysteine, nicotinamide riboside, resveratrol, NAD+ precursors, Coenzyme Q10, omega-3-fatty acids, cabbage powder, pterostilbene, and/or nicotinamide mononucleotide. Also included within the meaning of supplement ingredients are vitamins such as biotin (vitamin B7, vitamin H), choline (vitamin Bp), folate or folic acid (vitamin M), niacin (vitamin B3), pantothenic acid (vitamin B5), riboflavin (vitamin B2, vitamin G), thiamine (vitamin B1), retinol (vitamin A), pyridoxine, pyridoxamine, or pyridoxal (vitamin B6), cobalamin (vitamin B12), ascorbic acid (vitamin C), tocopherol (vitamin E), and naphthoquinoids (vitamin K). Supplement ingredients can further include dietary minerals such as, for example, chromium, or any or any pharmaceutically acceptable salts, hydrates, solvates, or mixtures thereof, bromine, cobalt, copper, fluorine, germanium, iodine, iron, magnesium, manganese, molybdenum, potassium, selenium, silicon, zinc, calcium, phosphorous, sodium, sulfur, and vanadium. Supplement ingredients can also comprise cranberry extract, turmeric, royal jelly, Kai berry, beet root, coral calcium, oyster shell, gotu kola, Gingko biloba, lions mane mushroom, pomegranate, hibiscus flower, strawberry powder, dandelion root, celery powder, parsley powder, peppermint leaf, cinnamon bark powder, maca root, and combinations thereof. Supplement ingredients can include nitrates such as citrulline nitrate, creatine nitrate, beta-alanine nitrate, and the like, as well as nitric oxide promoters. Compositions described herein can include one or more of the foregoing supplement ingredients, as would be understood by one of skill in the art.

In some embodiments, the compositions disclosed herein are administered daily, every other day, or multiple times per day. Some embodiments can utilize a ramping administration protocol where a subject is administered increasing amounts of compositions described herein. For example, a subject could be administered with 100 mg of a composition as described herein per day for 7 days, followed by 200 mg, for the next 7 days, followed by 300 mg for the next 7 days. Administration protocols can also follow a pattern whereby the dosage amount decreases over time. For example, 300 mg of a composition as described herein per day for 7 days, followed by 200 mg, for the next 7 days, followed by 100 mg for the next 7 days. In some embodiments, the methods described herein are utilized in combination with a calorie restriction protocol in a subject.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, the terms "prophylactic treatment," "prevent," or "preventing," can refer to treating a subject who does not yet exhibit symptoms of a disease or condition, but who is susceptible to, or otherwise at risk of, a particular disease or condition, whereby the treatment reduces the likelihood that the patient will develop the disease or condition. A "disorder" is any condition that would benefit from treatment with the compositions described herein.

As used herein, the terms "preventing", "treating", "treatment" and the like are used herein to generally refer to obtaining a desired pharmacological and physiological effect and can also refer to a nutritional or nutraceutical effect, the scopes, and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities. The terms "optimum" or "healthy" and the like may be used to refer to the physiological amounts of beta-adrenergic or muscarinic activity in a mammal, wherein administration of compositions as described herein may be administered to a mammal that may not have a disease or symptoms of a disease associated with beta-adrenergic or muscarinic activity, but may be administered to agonize beta-adrenergic receptors or antagonize muscarinic receptors along with the other physiological results described herein. Compositions described herein can be administered to subjects to support normal bladder function. Compositions described herein can be administered to subjects to maintain healthy levels of bladder activity and urinary frequency. Compositions described herein can be administered to maintain healthy levels of one or more of urinary urgency, urinary incontinence, urge incontinence, polyuria, nocturia, bladder spasms, and any combination thereof.

As used herein, the terms "selective binding," "selectively binding," and "selectivity" refer to the binding of a compound to a receptor, wherein the compound has a greater binding affinity for one subtype of the receptor relative to a different subtype of the same receptor. Examples of "selective binding," "selectively binding," and "selectivity" may be a compound that has a higher binding affinity for the M2 muscarinic receptor relative to the M1 muscarinic receptor, a higher binding affinity for the M3 muscarinic receptor relative to the M1 muscarinic receptor, a higher binding affinity for the M2 muscarinic receptor relative to the M4 muscarinic receptor, and a higher binding affinity for the M3 muscarinic receptor relative to the M4 muscarinic receptor. In light of this disclosure, "selective binding," "selectively binding," and "selectivity" may be derived by measuring the binding affinity of receptor subtypes, e.g., a dissociation constant, a binding percent relative to a control, and the like, taking a ratio between two relative receptor subtypes, and determining the value of said ratio. In light of this disclosure, "selective binding," "selectively binding," and "selectivity" ordinarily refers to when said ratio is at least 1, although this ratio can be referred to as "selective" when it is greater than 1, for which this will be clear to the skilled artisan based upon the context in which this term is used.

As used in the claims below and throughout this disclosure, the phrase "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of a composition" for the treatment of a particular disease or disorder, or the maintenance of a healthy condition, would exclude other ingredients that would materially alter the intended outcome of the composition.

As used herein, a composition that "substantially" comprises a compound means that the composition contains more than about 80% by weight, more preferably more than about 90% by weight, even more preferably more than about 95% by weight, and most preferably more than about 98% by weight of the compound.

The term "pharmaceutical formulation", "formulation", "composition" and the like can refer to preparations which are in such a form as to permit the biological activity of the active ingredients to be effective, and therefore may be administered to a subject for therapeutic use along with dietary and/or nutritional supplement use. The meaning of these terms will be clear to the skilled artisan based upon the context in which they are used.

A "therapeutically effective amount" as used herein includes within its meaning a non-toxic but sufficient amount of a compound active ingredient or composition comprising the same for use in the embodiments disclosed herein to provide the desired therapeutic effect. Similarly, "an amount effective to" or "an effective amount" as used herein includes within its meaning a non-toxic but sufficient amount of a compound active ingredient or composition comprising the same to provide the desired effect. A "therapeutically effective amount" or an "effective amount" includes amounts of compounds that would not be achievable through a standard diet, but requires supplementation and dosing, as described herein. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it may not always be possible to specify an exact "effective amount." However, for any given case, an appropriate "effective amount" may be determined by one of ordinary skill in the art in view of the disclosure contained herein. In some aspects, a therapeutically effective amount may include a dosing regimen. For example, a therapeutically effective amount may include about 100 mg of a composition orally consumed each day for fourteen consecutive days. In some aspects, a therapeutically effective amount may include about 100 mg of a composition orally consumed each day for thirty consecutive days. Compositions including a composition may include, for example, between 0.1-10,000 milligrams of the composition.

As used herein, the terms "synergy", "synergistic", "synergism" and the like are used herein to generally refer to the therapeutic efficacy of a composition being at least equal to the sum of the efficacy of the individual components in the composition administered independently. "Synergy", "synergistic", "synergism" and the like may also refer to the therapeutic efficacy of a composition being greater than to the sum of the efficacy of the individual components in the composition administered independently. The scopes and meanings of which will be clear to the skilled artisan based upon the context in which these terms are used.

As used herein, the terms "support bladder health" and "maintain normal bladder function" refer to support/maintain the ability to hold urine and empty bladder 4-7 times a day.

Unless otherwise indicated, when a property having units of mass (e.g., mg, g, kg, etc.), or describing a ratio of properties having units of mass (e.g., ratio, weight ratio, mass ratio, g/g, mg/kg, etc.), is recited, the units of mass are based on a dry basis. As used herein, the term "dry basis" refers to the mass of material wherein all solvent has been removed. For example, if a composition contains 100 mg of ground *Crataeva nurvala* leaves, the composition will contain 100 mg of dry ground *Crataeva nurvala* leaves. As another example, if a composition contains a 4:1 ratio of ground *Crataeva nurvala* leaves to SAMe, that composition may contain 400 mg of dry ground *Crataeva nurvala* leaves and 100 mg of SAMe powder, or 200 mg of dry ground *Crataeva nurvala* leaves and 50 mg of SAMe powder, etc. In certain embodiments, particular compositions may comprise extracts. In such instances, the extract may be obtained via aqueous or organic extraction of a plant material. The plant material from which the extract is obtained can be obtained from dried plant material or on an unaltered basis. In some embodiments, the extract may be able to form a powder. In these instances, the aforementioned dry basis would refer to the mass of the dried powder. In other instances, the extract may not be able to form a powder and may present as an oil. In these instances, the aforementioned dry basis would refer to the mass of the solvent-free oil, i.e., the mass of the oil upon removal of all solvent used to obtain said extract. As disclosed herein, embodiments may comprise compositions that are beta-adrenergic receptor agonists and/or muscarinic receptor antagonists. These compositions may constitute compounds and extracts thereof. For example, certain compositions may comprise phycocyanin as the muscarinic receptor antagonist, whereas other compositions may comprise an extract of phycocyanin as the muscarinic receptor antagonist. A person having ordinary skill in the art would understand how to make an extract of phycocyanin and use this extract as a muscarinic receptor antagonist to achieve the results presented herein. In certain embodiments, an extract of phycocyanin may refer to a composition that is synthesized or formulated from a phycocyanin starting material, wherein the extract is created to have a specific compositional characteristics.

In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered as the sole treatment or in conjunction with other drugs or therapies useful in treating the condition in question.

By way of example, a "therapeutically effective amount" and/or an "effective amount" of the compound disclosed herein can be (on a dosage weight per subject weight basis), for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300

µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg·kg, 2.0 mg/kg, 2.5 mg/kg, 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, or more, or any fraction or integer in between any two of the preceding amounts of the compound. An effective amount may include any of the ranges and amounts discussed herein.

Accordingly, in some embodiments, the dose of the compound in compositions disclosed herein can be about 10 µg to about 10 g, preferably per day. For example, the amount of the composition can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any range or amount in between any two of the preceding values and any other ranges or amounts disclosed herein. The exemplary therapeutically effective amounts listed above, can, in some embodiments be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

In some embodiments, the composition, dietary supplement, and/or pharmaceutical agent may comprise one or more beta-adrenergic receptor agonists, one or more muscarinic receptor antagonists, or a combination thereof presented in a synergistic ratio. In some embodiments the beta-adrenergic receptor is a SAMe composition or a SAMe and PG composition. In some embodiments the muscarinic receptor antagonist is a pumpkin seed composition, a *Crataeva nurvala* composition, a *Lindera aggregata* composition, a black and/or yellow maca composition, a phycocyanin composition, or any combination of the foregoing. In some embodiments, the synergistic ratio can comprise about 2:2:1 of a pumpkin seed composition to a *Crataeva nurvala* composition to a *Lindera aggregata* composition (P+C+L). In some embodiments, the P+C+L synergistic ratio can comprise any ratio between about 10:1:1 to about 1:10:1 to about 1:1:10. In some embodiments, the synergistic ratio can comprise about 1:0.5 of P+C+L to a black and/or yellow maca composition. In some embodiments, the P+C+L to the black and/or yellow maca composition synergistic ratio can comprise any ratio between about 10:1 to about 1:10. In some embodiments, the synergistic ratio can comprise about 1:0.5 of P+C+L to a phycocyanin composition. In some embodiments, the P+C+L to the phycocyanin composition synergistic ratio can comprise any ratio between about 10:1 to about 1:10. In some embodiments, the synergistic ratio can comprise about 1:0.5 of P+C+L to a SAMe composition. In some embodiments, the synergistic ratio can comprise about 1:0.5 of P+C+L to a SAMe and PG composition. In some embodiments, the P+C+L to the SAMe composition synergistic ratio can comprise any ratio between about 10:1 to about 1:10. In some embodiments, the P+C+L to the SAMe and PG composition synergistic ratio can comprise any ratio between about 10:1 to about 1:10. In some embodiments, the synergistic ratio can comprise about 4:1:3.2 of a *Crataeva nurvala* composition to a black and/or yellow maca composition to a SAMe composition. In some embodiments, the synergistic ratio can comprise about 4:1:3.2 of a *Crataeva nurvala* composition to a black and/or yellow maca composition to a SAMe and PG composition. In some embodiments, the synergistic ratio can comprise about 1.6:2.5:1 of a *Crataeva nurvala* composition to a black and/or yellow maca composition to a SAMe composition. In some embodiments, the synergistic ratio can comprise about 1.6:2.5:1 of a *Crataeva nurvala* composition to a black and/or yellow maca composition to a SAMe and PG composition. In some embodiments, the synergistic ratio can comprise about 4:1:1.5 of a *Crataeva nurvala* composition to a black and/or yellow maca composition to a SAMe composition. In some embodiments, the synergistic ratio can comprise about 4:1:1.5 of a *Crataeva nurvala* composition to a black and/or yellow maca composition to a SAMe and PG composition. In some embodiments, the *Crataeva nurvala* composition to black and/or yellow maca composition to the SAMe composition synergistic ratio can comprise any ratio between about 2:1:1 to about 1:2:1. In some embodiments, the *Crataeva nurvala* composition to black and/or yellow maca composition to the SAMe and PG composition synergistic ratio can comprise any ratio between about 2:1:1 to about 1:2:1. In some embodiments, the *Crataeva nurvala* composition to black and/or yellow maca composition to the SAMe composition synergistic ratio can comprise any ratio between about 4:1:1 to about 4:1:4. In some embodiments, the *Crataeva nurvala* composition to black and/or yellow maca composition to the SAMe and PG composition synergistic ratio can comprise any ratio between about 4:1:1 to about 4:1:4. In some embodiments, the synergistic ratio can comprise about 1:1 of a *Crataeva nurvala* composition to a SAMe composition. In some embodiments, the synergistic ratio can comprise about 1:1 of a *Crataeva nurvala* composition to a SAMe and PG composition. In some embodiments, the synergistic ratio can comprise about 2.3:1 of a *Crataeva nurvala* composition to a SAMe composition. In some embodiments, the synergistic ratio can comprise about 2.3:1 of a *Crataeva nurvala* composition to a SAMe and PG composition. In some embodiments, the synergistic ratio can comprise about 2.4:1 of a *Crataeva nurvala* composition to a SAMe composition. In some embodiments, the synergistic ratio can comprise about 2.4:1 of a *Crataeva nurvala* composition to a SAMe and PG composition. In some embodiments, the *Crataeva nurvala* composition to the SAMe composition synergistic ratio can comprise any ratio between about 10:1 to about 1:10. In some embodiments, the *Crataeva nurvala* composition to the SAMe and PG composition synergistic ratio can comprise any ratio between about 10:1 to about 1:10. In some embodiments, the *Crataeva nurvala* composition to the SAMe composition synergistic ratio can comprise any ratio between about 2:1 to about 3:1. In some embodiments, the *Crataeva nurvala* composition to the SAMe and PG composition synergistic ratio can comprise any ratio between about 2:1 to about 3:1.

The present disclosure comprises nutritional and therapeutic compositions useful as a beta-adrenergic receptor agonist or muscarinic receptor antagonists, and methods of using the same. Some embodiments provide solid dosage forms of the compositions disclosed herein. Some embodiments provide aqueous solutions of compositions disclosed herein. Embodiments described herein comprising compositions disclosed herein as a nutritional supplement means that the composition disclosed herein is present in an unnatural form, i.e., is presented in a supplement (e.g., in a pill or powder) that is different from that which occurs naturally, or the nutritional or dietary supplement results in unnatural supplementation that is unachievable through a non-supplemented diet.

Some embodiments provide physiologically compatible compositions as disclosed herein including hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit, microcrystalline cellulose, hydroxypropylmethylcellulose phthalate, and the like.

As used herein, the term "pharmaceutically acceptable solvent" can refer to water, water for injection, aqueous buffer solutions that are physiologically compatible, or aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997 or its current issue.

As used herein, the term "bioavailability" refers to the amount of a substance that is absorbed in the intestines and ultimately available for biological activity in a subject's tissue and cells.

As used herein, the term "enhancing the bioavailability" and the like are used herein to refer to obtaining a desired pharmacological and/or physiological effect of agonizing a beta-adrenergic receptor, antagonizing a muscarinic receptor, or both, that is absorbed from the intestine or is taken up by tissues and cells after administration of a composition to a mammal, which does not occur naturally. The effect may be prophylactic in terms of preventing or partially preventing the incidence, risk, or severity of an adverse symptom or condition caused by or related to the deficiency of a therapeutic agent.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For the purpose of this disclosure, a warm-blooded animal is a member of the animal kingdom which includes but is not limited to mammals and birds. In certain embodiments described herein, a mammal may, for example but without limitation, be a horse, dog, or cat. The most preferred mammal of this application is human.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin, or acacia; and lubricating agents such as magnesium stearate, stearic acid, or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin, or olive oil. Aqueous suspensions can contain the complex of the described herein admixed with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the active ingredient in admixture with a dispersing or wetting agent, a suspending agent, and one or more preservatives. Additional excipients, for example sweetening, flavoring, and coloring agents, can also be present.

Syrups and elixirs can be formulated with sweetening agents, such as glycerol, sorbitol, or sucrose. Such formulations can also contain a demulcent, a preservative, a flavoring, or a coloring agent.

The composition for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution, and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

It will be appreciated that the amount of the compound may be combined with a carrier material to produce a single dosage form. Such forms will vary depending upon the host treated and the particular mode of administration.

In some embodiments, compositions described herein may be administered via supplements or dosages designed for animals. In some animal applications, the compound or composition may be added to and/or comprise a pet treat or biscuit, for example, a dog biscuit or a cat treat.

Aqueous suspensions may contain the compound disclosed herein in admixture with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Utilization of controlled release vehicles would readily be envisaged by those of skill in the pharmaceutical sciences in view of the disclosure contained herein, and these aspects can be applied to nutritional and dietary supplements. The technology and products in this art are variably referred to as controlled release, sustained release, prolonged action, depot, repository, delayed action, retarded release, and timed release; the words "controlled release" as used herein is intended to incorporate each of the foregoing technologies.

Numerous controlled release vehicles can be used, including biodegradable or bioerodable polymers such as polylactic acid, polyglycolic acid, and regenerated collagen. Controlled release drug delivery devices can include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, and can be used in the disclosed methods.

Controlled release preparations can be achieved by the use of polymers to form complexes with or absorb a composition. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes refers to any of the extended release dosage forms known in the art or described herein. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein a composition as disclosed herein is dissolved in an aqueous constituent to gradually release over time, can be prepared by copolymerization of hydrophilic mono-olefinic monomers such as ethylene glycol methacrylate. Matrix devices, wherein a composition is dispersed in a matrix of carrier material, can be used. The carrier can be porous, non-porous, solid, semi-solid, permeable, or impermeable. Alternatively, a device comprising a central reservoir of a composition disclosed herein surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations can also be used in embodiments described herein. In an embodiment, a composition as described herein is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Compositions described herein may be administered once, twice, or three times per day. In some embodiments, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. In one aspect, the embodiments described herein can achieve therapeutic and/or nutraceutical benefits not previously recognized or achievable, and thus, unexpectedly, and surprisingly achieve improved abilities for using the compositions. In some embodiments a composition is formulated for intravenous administration because a more concentrated solution can be produced. Whether the active agents of the therapy are administered by oral or intravenous route, separately or together, each such active agent will be contained in a suitable pharmaceutical formulation of pharmaceutically-acceptable excipients, diluents, or other formulations components.

Active ingredients (i.e., compositions disclosed herein that may be combined with other pharmaceutical or supplemental ingredients that may be present) can be administered by the oral route in solid dosage forms, such as tablets, capsules, and powders, or in liquid dosage forms, such as elixirs, syrups, and suspensions. Each active ingredient can be administered by the parenteral route in liquid dosage forms. The composition can be made in the form of a dosage unit containing a particular amount of each active ingredient. One example of an oral dosage form of a composition of the present application is an admixture of powders contained within a sachet. Because a composition of the present application is not hygroscopic and has no repugnant taste or odor, the admixture of powders comprising a composition of the present application can be sprinkled on food or stirred into beverages to enhance ease of use and support high levels of compliance with daily dosage regimens.

In general, the dosage forms of compositions of this disclosure can be prepared by techniques described in Remington's Pharmaceutical Sciences, a reference in this field [Gennaro AR, Ed. Remington: The Science and Practice of Pharmacy. 20th Edition. Baltimore: Lippincott, Williams & Williams, 2000]. For therapeutic purposes, the active components of this combination therapy application can be combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration, the amounts of which are ascertainable by the skilled artisan. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration can be utilized, and these aspects can also be applied to any of the nutritional or dietary supplements described herein.

EXAMPLES

Example 1

The muscarinic receptor antagonist activity of compositions disclosed herein were determined by a G-coupled protein receptor (GPCR) arrestin assay, commercially available as the PathHunter® β-arrestin assay.

Cell lines were expanded from freezer stocks according to standard procedures. Cells were then seeded in a total volume of 20 µL into white walled, 384-well microplates and incubated at 37° C. for the appropriate time prior to testing. Cells were pre-incubated with antagonist followed by agonist challenge at the EC80 concentration. Stock solutions of the muscarinic receptor antagonists were prepared at concentration ranging from 0.05-1000 mg/ml. Intermediate dilution of sample stocks was performed to generate 5× sample in assay buffer. 5 µL of 5× sample was added to cells and incubated at 37° C. or room temperature for 30 minutes. Vehicle concentration was 1%. 5 µL of 6× EC80 agonist in assay buffer was added to the cells and incubated at 37° C. or room temperature for 90 or 180 minutes. Assay signal was generated through a single addition of 12.5 or 15 µL (50% v/v) of Detection reagent cocktail, followed by a one-hour incubation at room temperature. Microplates were read following signal generation with a PerkinElmer Envision™ instrument for chemiluminescent signal detection. Compound activity was analyzed using CBIS data analysis suite (ChemInnovation, CA). Percentage inhibition was calculated using the following formula:

% Inhibition=100%×(1−(mean RLU of test sample−mean RLU of vehicle control)/(mean RLU of EC80 control−mean RLU of vehicle control)).

The results, as shown in FIG. 1, are expressed as a maximum percent binding of the muscarinic receptors: M1 (solid fill), M2 (empty fill), M3 (diagonal fill), M4 (horizontal fill), and M5 (cross-hatch fill), relative to controls—acetylcholine, a muscarinic receptor agonist, and atropine, a muscarinic receptor antagonist, (data not shown), upon the administration of a dose range of 0.05-1000 µg of a pumpkin seed composition (P), a *Crataeva nurvala* composition (C), a *Lindera aggregata* composition (L), a 1:1 mixture of black (B) and yellow (Y) maca, and a phycocyanin composition in vitro.

FIG. 1 shows superior and unexpected M2 and M3 muscarinic receptor antagonism achieved by administration of various compositions, including the *Crataeva nurvala* composition (C), the *Lindera aggregata* composition (L), the 1:1 mixture of black (B) and yellow (Y) maca, and the phycocyanin composition, expressed as receptor binding (%), and were 45.6%, 21.9%, 35.4%, and 16.1%, respectively for M2, and 24.2%, 0.3%, 16.0%, and 1.3%, respectively for M3.

Figure 3:
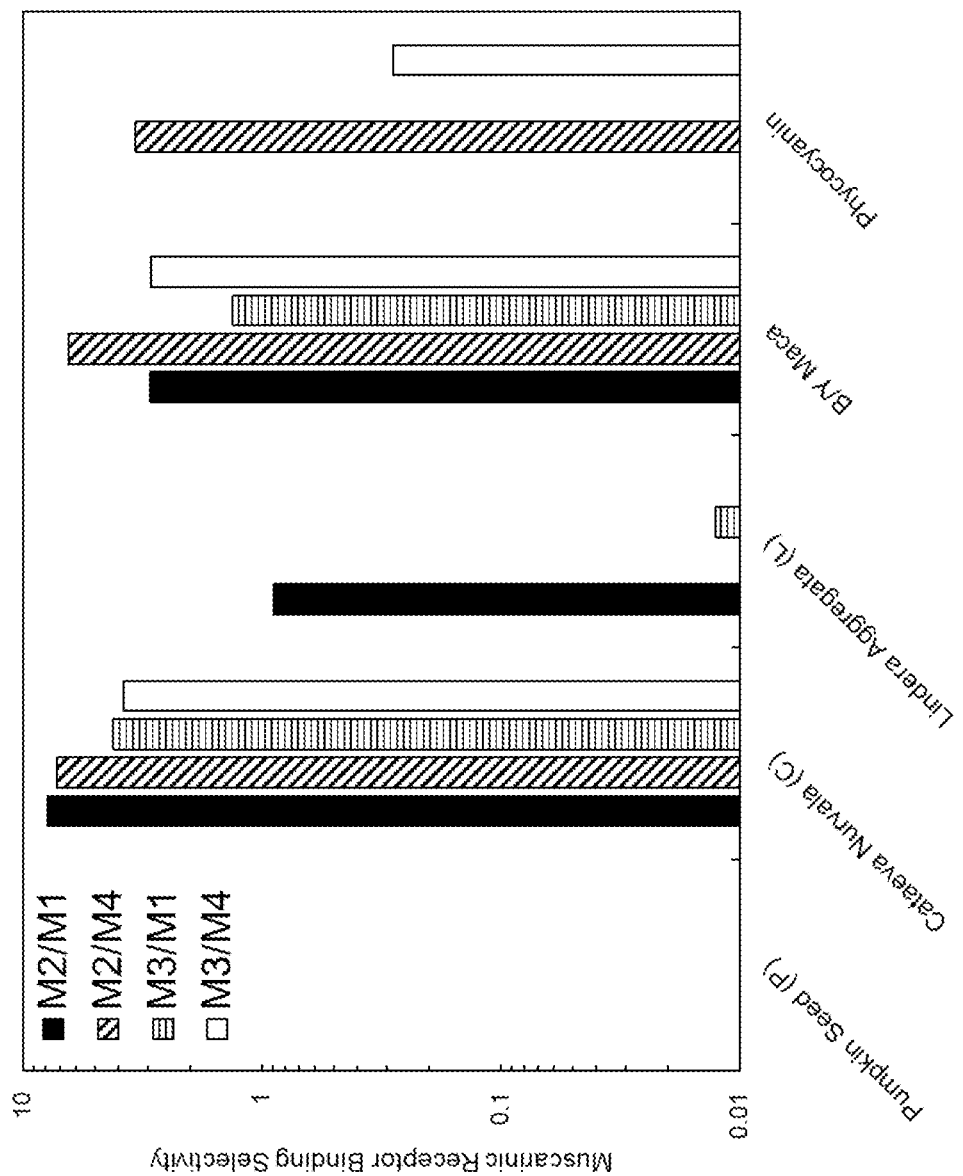
FIG. 3 shows the relative binding selectivity for the M1-M4 muscarinic receptors at maximum binding for a pumpkin seed composition (P), a *Crataeva nurvala* composition (C), a *Lindera aggregata* composition (L), a 1:1 mixture of black (B) and yellow (Y) maca, and a phycocyanin composition, according to one or more embodiments of the disclosure, for a dose range of 0.05-1000 µg evaluated in vitro. The series are: M2/M1 selectivity (solid), M2/M4 selectivity (diagonal fill), M3/M1 selectivity (horizontal fill), and M3/M4 selectivity (empty fill)

The results from FIG. 1 were transformed to express the binding selectivity for the muscarinic receptor antagonists, as shown in FIG. 3. The maximum binding selectivity of M2/M1 (solid fill), M2/M4 (diagonal fill), M3/M1 (horizontal fill), and M3/M4 (empty fill) were obtained for a pumpkin seed composition (P), a *Crataeva nurvala* composition (C), a *Lindera aggregata* composition (L), a 1:1 mixture of black (B) and yellow (Y) maca, and a phycocyanin composition.

FIG. 3 shows superior and unexpectedly selective binding for the M2 and M3 muscarinic receptors relative to the M1 and M4 muscarinic receptors achieved by administration of various compounds; specifically, both the *Crataeva nurvala* composition (C) and the 1:1 mixture of black (B) and yellow (Y) maca demonstrated high selectivity (>1) for the M2 and M3 muscarinic receptors relative to the M1 and M4 muscarinic receptors, and the phycocyanin composition demonstrated a high selectivity for the M2 muscarinic receptor relative to the M4 muscarinic receptor.

Example 2

Figure 2:
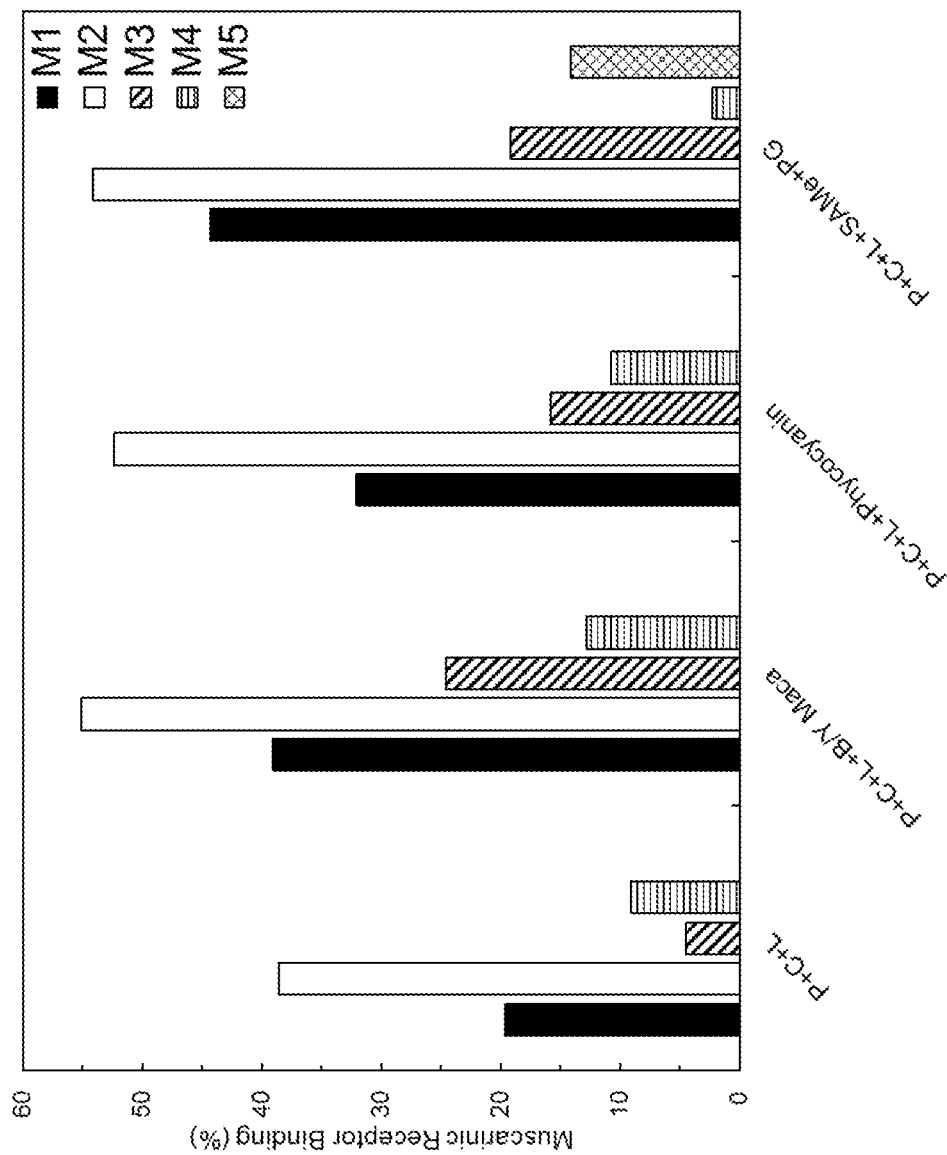
FIG. 2 shows the maximum binding percentage for the muscarinic receptors: M1 (solid fill), M2 (empty fill), M3 (diagonal fill), M4 (horizontal fill), and M5 (cross-hatch fill) of a 2:2:1 mixture of a pumpkin seed composition, a *Crataeva nurvala* composition, and a *Lindera aggregata* composition (P+C+L), a 2:2:1:0.5 mixture of a pumpkin seed composition, a *Crataeva nurvala* composition, a *Lindera aggregata* composition, and a 1:1 mixture of black (B) and yellow (Y) maca (P+C+L+B/Y Maca), a 2:2:1:0.5 mixture of a pumpkin seed composition, a *Crataeva nurvala* composition, a *Lindera aggregata* composition, and a phycocyanin composition (P+C+L+Phycocyanin), and a 2:2:1:0.5 mixture of a pumpkin seed composition, a *Crataeva nurvala* composition, a *Lindera aggregata* composition, and a 32:1 mixture of s-adenosyl-L-methionine (SAMe) and propyl gallate (PG) (P+C+L+SAMe+PG), according to one or more embodiments of the disclosure, for a dose range of 0.05-1000 µg evaluated in vitro.

The experimental procedure of Example 2 is the same procedure and analysis as described in Example 1. In Example 2, the treatments were adjusted to evaluate combinations the following compositions: a 2:2:1 mixture of a pumpkin seed composition, a *Crataeva nurvala* composition, and a *Lindera aggregata* composition (P+C+L), a 2:2:1:0.5 mixture of a pumpkin seed composition, a *Crataeva nurvala* composition, a *Lindera aggregata* composition, and 1:1 mixture of black (B) and yellow (Y) maca (P+C+L+B/Y Maca), a 2:2:1:0.5 mixture of a pumpkin seed composition, a *Crataeva nurvala* composition, a *Lindera aggregata* composition, and a phycocyanin composition (P+C+L+Phycocyanin), and a 2:2:1:0.5 mixture of a pumpkin seed composition, a *Crataeva nurvala* composition, a *Lindera aggregata* composition, and a 32:1 mixture of SAMe and PG (P+C+L+SAMe+PG), for a dose range of 0.05-1000 µg. The results in FIG. 2 show the maximum binding percentage for the muscarinic receptors: M1 (solid fill), M2 (empty fill), M3 (diagonal fill), M4 (horizontal fill), and M5 (cross-hatch fill) for the aforementioned compositions.

FIG. 2 shows superior and unexpected M2 and M3 muscarinic receptor antagonism compared to prior art formulations, which is achieved by administration of various compounds, including the mixture of the pumpkin seed composition, the *Crataeva nurvala* composition, and the *Lindera aggregata* composition (P+C+L), the mixture of P+C+L and the 1:1 mixture of black (B) and yellow (Y) maca (P+C+L+B/Y Maca), the mixture of P+C+L and the phycocyanin composition (P+C+L+Phycocyanin), the mixture of P+C+L and the SAMe and PG (P+C+L+SAMe+PG), expressed as receptor binding (%), and were 38.6%, 55.1%, 52.4%, and 54.2%, respectively for M2, and 4.5%, 24.6%, 15.9%, and 19.2%, respectively for M3.

Figure 4:
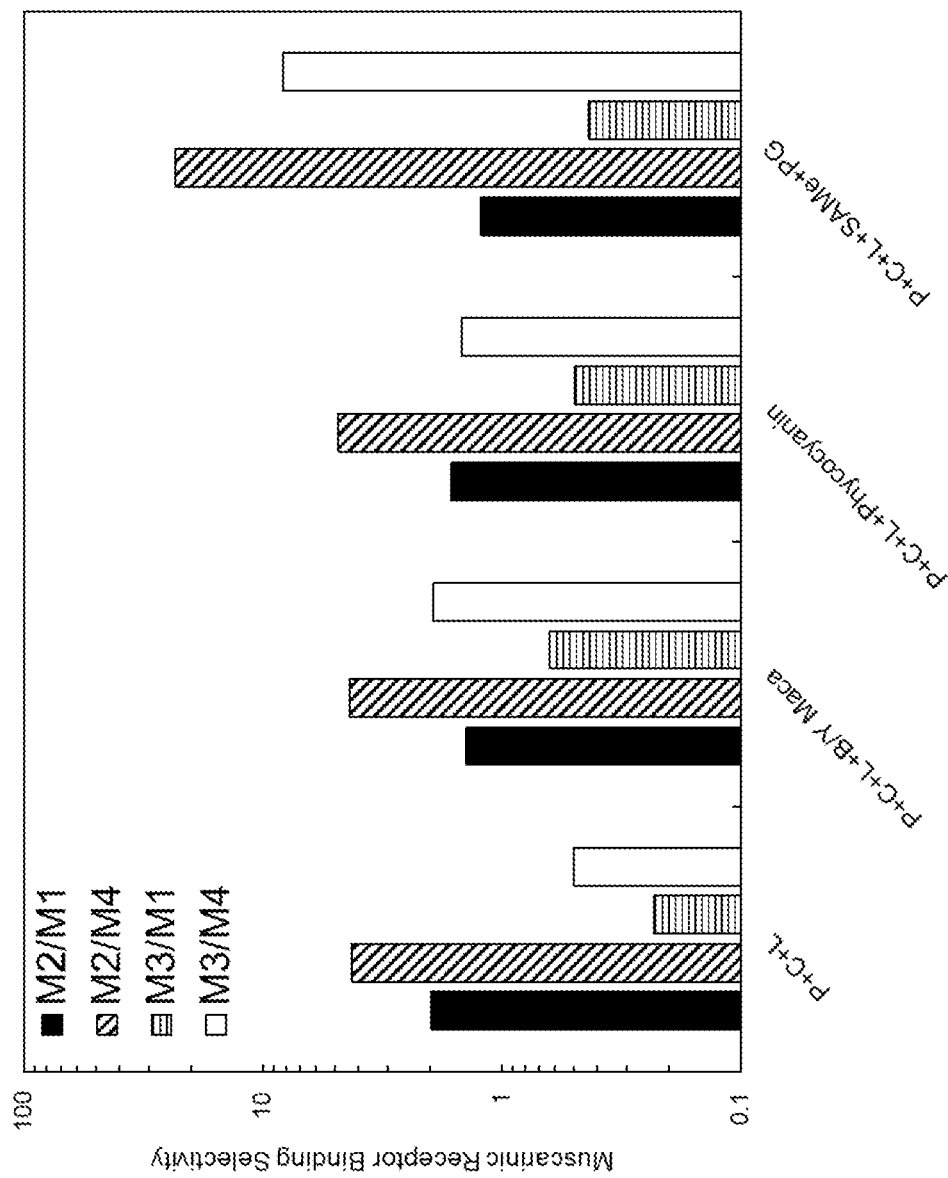
FIG. 4 shows the relative binding selectivity for the M1-M4 muscarinic receptors at maximum binding for a 2:2:1 mixture of a pumpkin seed composition, a *Crataeva nurvala* composition, and a *Lindera aggregata* composition (P+C+L), a 2:2:1:0.5 mixture of a pumpkin seed composition, a *Crataeva nurvala* composition, a *Lindera aggregata* composition, and 1:1 mixture of black (B) and yellow (Y) maca (P+C+L+B/Y Maca), a 2:2:1:0.5 mixture of a pumpkin seed composition, a *Crataeva nurvala* composition, a *Lindera aggregata* composition, and a phycocyanin composition (P+C+L+Phycocyanin), and a 2:2:1:0.5 mixture of a pumpkin seed composition, a *Crataeva nurvala* composition, a *Lindera aggregata* composition, and 32:1 mixture of SAMe and PG (P+C+L+SAMe+PG), according to one or more embodiments of the disclosure, for a dose range of 0.05-1000 µg evaluated in vitro. The series are: M2/M1 selectivity (solid), M2/M4 selectivity (diagonal fill), M3/M1 selectivity (horizontal fill), and M3/M4 selectivity (empty fill).

The results from FIG. 2 were transformed to express the binding selectivity for the muscarinic receptor antagonists, as disclosed herein, and shown in FIG. 4. The maximum binding selectivity of: M2/M1 (solid fill), M2/M4 (diagonal fill), M3/M1 (horizontal fill), and M3/M4 (empty fill), were obtained for a 2:2:1 mixture of a pumpkin seed composition, a *Crataeva nurvala* composition, and a *Lindera aggregata* composition (P+C+L), a 2:2:1:0.5 mixture of a pumpkin seed composition, a *Crataeva nurvala* composition, a *Lindera aggregata* composition, and a 1:1 mixture of black (B) and yellow (Y) maca (P+C+L+B/Y Maca), a 2:2:1:0.5 mixture of a pumpkin seed composition, a *Crataeva nurvala* composition, a *Lindera aggregata* composition, and a phycocyanin composition (P+C+L+Phycocyanin), and a 2:2:1:0.5 mixture of a pumpkin seed composition, a *Crataeva nurvala* composition, a *Lindera aggregata* composition, and a 32:1 mixture of SAMe and PG (P+C+L+SAMe+PG).

FIG. 4 shows superior and unexpectedly selective binding for the M2 and M3 muscarinic receptors relative to the M1 and M4 muscarinic receptors achieved by administration of various compounds, which demonstrates a novel improvement over the prior art; specifically, for M2 relative to M1 and M4, all combinations demonstrated unexpectedly high selectivity (>1), for M3 relative to M4, P+C+L+B/Y Maca, P+C+L+Phycocyanin, and P+C+L+SAMe+PG demonstrated unexpectedly high selectivity (>1).

Example 3

The beta-adrenergic agonistic activity of compositions disclosed herein were evaluated with a cAMP assay, commercially available as the HitHunter® cAMP assay.

Cell lines were expanded from freezer stocks according to standard procedures. Cells were then seeded in a total volume of 20 µL into white walled, 384-well microplates and incubated at 37° C. for the appropriate time prior to testing. Cells were treated with 5 µL of 3× agonist solution prepared from stock solutions. Stock solutions of the beta-adrenergic agonists were prepared at concentration ranging from 5-1000 µg/ml. Intermediate dilution of sample stocks was performed to generate 3× sample in assay buffer. The cells were then incubated at 37° C. or room temperature for 90 or 180 minutes. Assay signal was generated through a single addition of 12.5 or 15 µL (50% v/v) of Detection reagent cocktail, followed by a one-hour incubation at room temperature. 20 µL of cAMP solution was then added, and the cells were incubated for 180 minutes at room temperature. Microplates were read following signal generation with a PerkinElmer Envision™ instrument for chemiluminescent signal detection. The EC50 was determined by known methods by reference the agonist reference curve.

Figure 5:
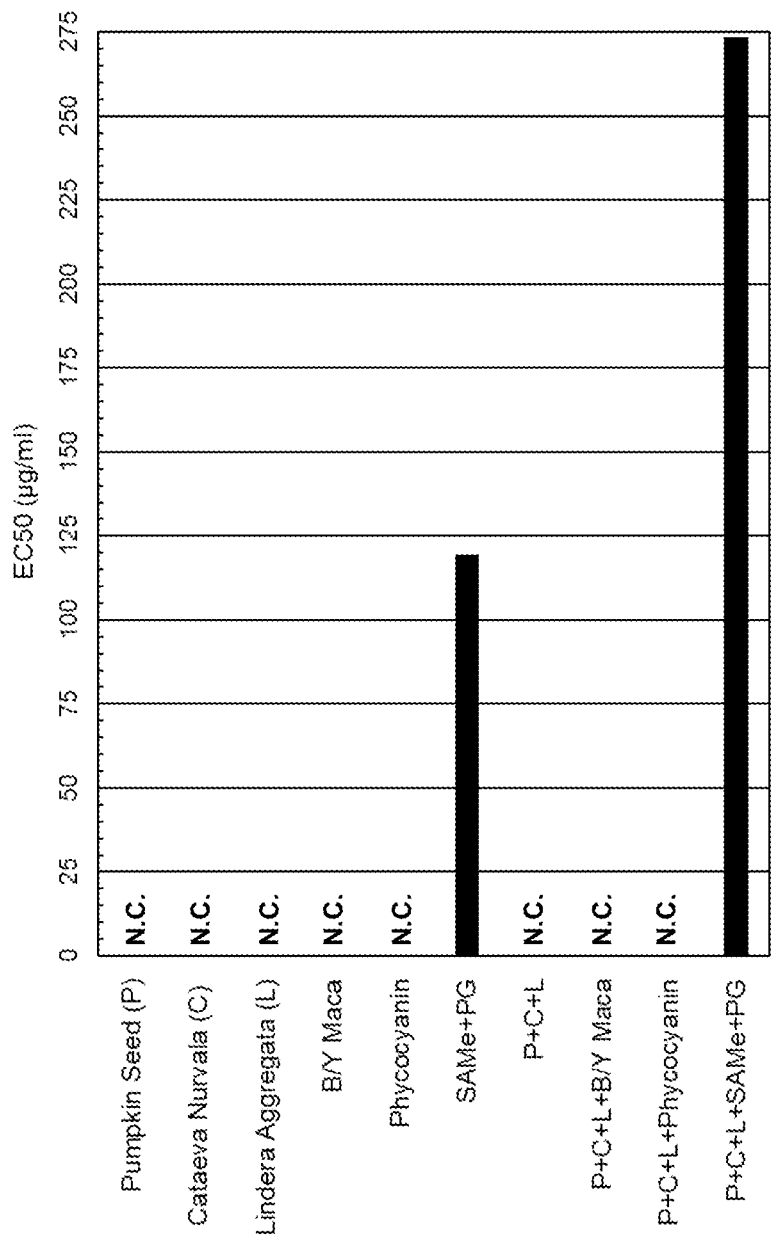
FIG. 5 shows the $EC_{50}$ values for (1) a pumpkin seed composition (P), (2) a *Crataeva nurvala* composition (C), (3) a *Lindera aggregata* composition (L), (4) a 1:1 mixture of black (B) and yellow (Y) maca, (5) a phycocyanin composition, (6) a 32:1 mixture of SAMe and PG, (7) a 2:2:1 mixture of a pumpkin seed composition, a *Crataeva nurvala* composition, and a *Lindera aggregata* composition (P+C+L), (8) a 2:2:1:0.5 mixture of a pumpkin seed composition, a *Crataeva nurvala* composition, a *Lindera aggregata* composition, and a 1:1 mixture of black (B) and yellow (Y) maca (P+C+L+B/Y Maca), (9) a 2:2:1:0.5 mixture of a pumpkin seed composition, a *Crataeva nurvala* composition, a *Lindera aggregata* composition, and a phycocyanin composition (P+C+L+Phycocyanin), and (10) a 2:2:1:0.5 mixture of a pumpkin seed composition, a *Crataeva nurvala* composition, a *Lindera aggregata* composition, and a 32:1 mixture of SAMe and PG (P+C+L+(SAMe & Propyl gallate)), according to one or more embodiments of the disclosure, as beta-adrenergic receptor agonists evaluated over a concentration range of 5-1000 µg/mL in vitro.

The results, as shown in FIG. 5, are expressed as an EC50 (µg/ml) value for a beta-adrenergic receptor, upon the administration of a dose range of 5-1000 µg/ml of (1) a pumpkin seed composition (P), (2) a *Crataeva nurvala* composition (C), (3) a *Lindera aggregata* composition (L), (4) a 1:1 mixture of black (B) and yellow (Y) maca, (5) a phycocyanin composition, (6) a 32:1 mixture of SAMe and PG, (7) a 2:2:1 mixture of a pumpkin seed composition, a *Crataeva nurvala* composition, and a *Lindera aggregata* composition (P+C+L), (8) a 2:2:1:0.5 mixture of a pumpkin seed composition, a *Crataeva nurvala* composition, a *Lindera aggregata* composition, and a 1:1 mixture of black (B) and yellow (Y) maca (P+C+L+B/Y Maca), (9) a 2:2:1:0.5 mixture of a pumpkin seed composition, a *Crataeva nurvala* composition, a *Lindera aggregata* composition, and a phycocyanin composition (P+C+L+Phycocyanin), and (10) a 2:2:1:0.5 mixture of a pumpkin seed composition, a *Crataeva nurvala* composition, a *Lindera aggregata* composition, and a 32:1 mixture of SAMe and PG (P+C+L+SAMe+PG). The only EC50 values were obtained were for the 32:1 mixture of SAMe and PG and the 2:2:1:0.5 mixture of a pumpkin seed composition, a *Crataeva nurvala* composition, a *Lindera aggregata* composition, and 32:1 mixture of SAMe and PG, which were 119.5 µg/ml and 273.4 µg/ml, respectively.

Example 4

An open-label, twelve-week clinic trial was conducted to determine the efficacy of a composition described herein, i.e., a combination of a beta-adrenergic agonist and muscarinic antagonists, in treating overactive bladder symptoms in women, as compared to the efficacy of a composition comprising muscarinic antagonists but not a beta-adrenergic agonist. An exemplary composition ("Composition 1") described herein was used, which comprises 200 mg of SAMe, 360 mg of *Crataeva nurvala* dry bark powder, and 250 mg of yellow maca dry root powder (shown in FIGS. 6-18 as "SAMe"). A composition used for comparison ("Composition 2") comprised 360 mg of *Crataeva nurvala* dry bark powder and 250 mg of yellow maca dry root powder (shown in FIGS. 6-18 as "No-SAMe").

Six peri-menopausal and nineteen post-menopausal women experiencing overactive bladder symptoms with an average age of 55.6 years old and an average weight of 153 pounds were randomly divided into two groups. A group of thirteen participants was orally administered with Composition 1 and the other group of twelve participants was orally administered Composition 2, twice a day with 8 oz of water, one in the morning upon waking and the other in the noon 30 minutes before a lunch.

Prior to the oral administration of Composition 1 and Composition 2, five overactive bladder symptoms experienced by each participant, i.e., daytime frequency, nocturia, daytime urgency, nighttime urgency, and daytime urge incontinence, were assessed and used as baselines. During the 12-week treatment, overactive bladder symptoms were recorded daily using online dairy. Changes of the five overactive bladder symptoms from the baselines were calculated. The results are shown in FIGS. 6-10. In addition, scores of overactive bladder symptom (OABS; ranging from 0 to 15 points with 0-2 points indicating no OAB symptoms, 3-5 points indicating mild OAB symptoms, 6-11 points indicating moderate OAB symptoms, and 12-15 points indicating severe OAB symptoms (Homma et al., 2006), the scores are the sum of scores as shown in Table 1 below), symptom bother, sleep, health-related quality of life (HRQL), daytime micturitions, nocturia, urgency, and urge incontinence were determined prior to the treatment (baseline) and during the 12-week treatment period. The percentage score changes from the baselines were calculated and are shown in FIGS. 11-18. The OABS scores are shown in Table 2.

TABLE 1

Determination of OAB Symptom Scores

| Question | Score | Frequency |
|---|---|---|
| How many times do you typically urinate from waking in the morning until sleeping at night? | 0 | 7 or less |
|  | 1 | 8-14 |
|  | 2 | 15 or more |
| How many times do you typically wake up to urinate from sleeping at night until waking in the morning? | 0 | 0 |
|  | 1 | 1 |
|  | 2 | 2 |
|  | 3 | 3 or more |
| How often do you have a sudden desire to urinate, which is difficult to defer? | 0 | Not at all |
|  | 1 | Less than once a week |
|  | 2 | Once a week or more |
|  | 3 | About once a day |
|  | 4 | 2-4 times a day |
|  | 5 | 5 times a day or more |
| How often do you leak urine because you cannot defer the sudden desire to urinate? | 0 | Not at all |
|  | 1 | Less than once a week |
|  | 2 | Once a week or more |
|  | 3 | About once a day |
|  | 4 | 2-4 times a day |
|  | 5 | 5 times a day or more |

Figure 6:
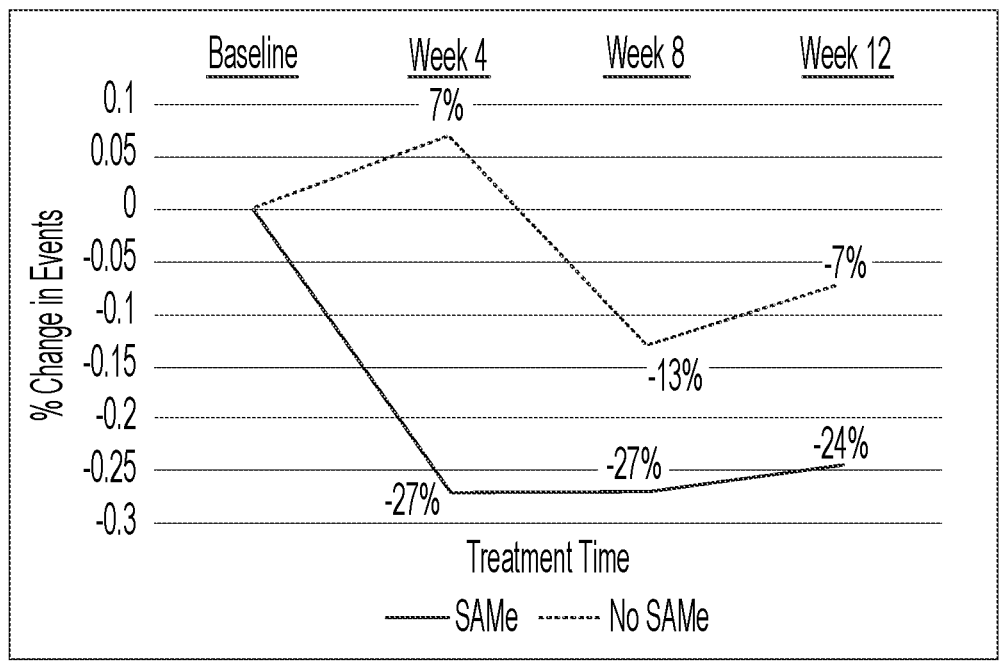
FIG. 6 shows daytime frequency changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 6 shows that daytime frequency in the group treated with Composition 1 decreased 27% at week 4 and such a decreased frequency remained at week 12. By contrast, daytime frequency in the group treated with Composition 2 slightly increased 7% at week 4 and decreased only 13% at week 8.

Figure 7:
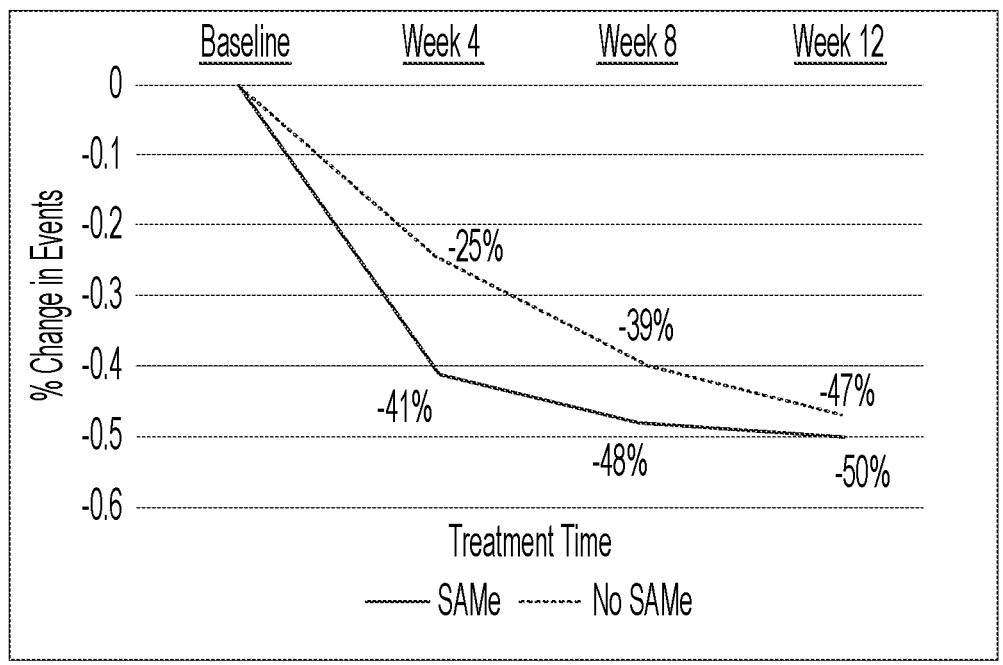
FIG. 7 shows nocturia changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of black and yellow maca.

FIG. 7 shows that nocturia in the group treated with Composition 1 decreased 41% at week 4. Differently, nocturia in the group treated with Composition 2 decreased only 25% at week 4.

Figure 8:
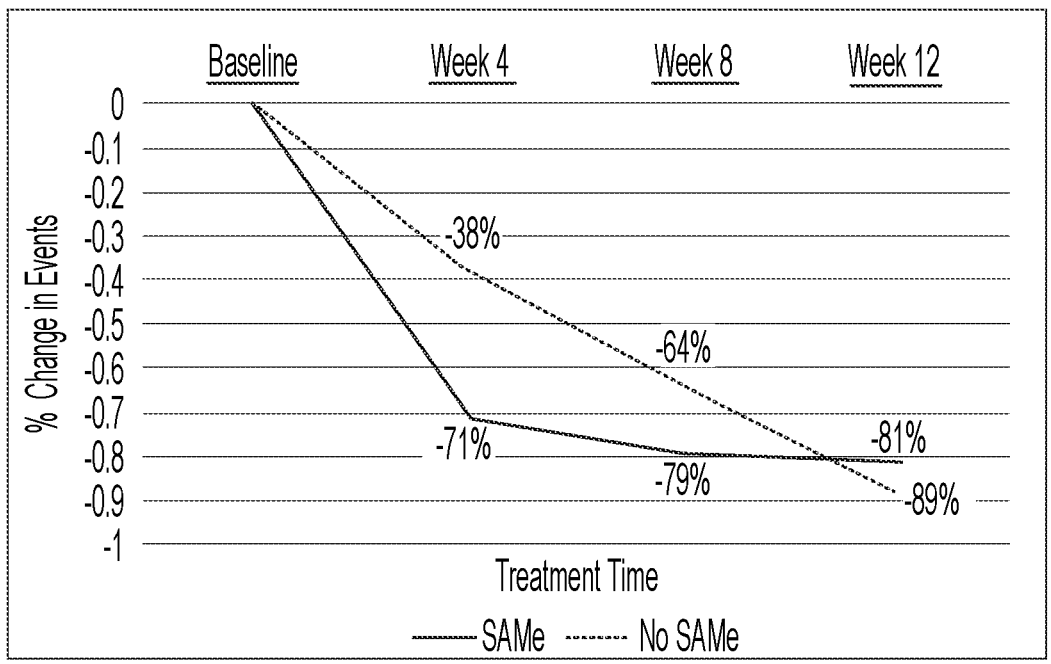
FIG. 8 shows daytime urgency changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 8 shows that daytime urgency in the group treated with Composition 1 decreased 71% at week 4, while daytime urgency in the group treated with Composition 2 decreased only 38% at week 4.

Figure 9:
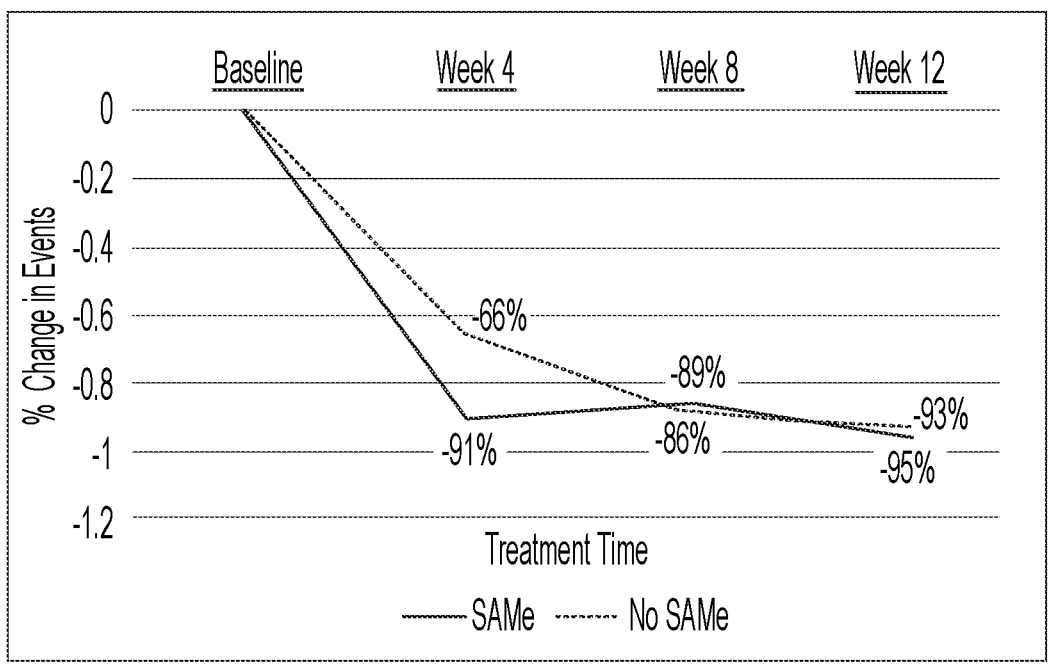
FIG. 9 shows nighttime urgency changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 9 shows that nighttime urgency in the group treated with Composition 1 decreased 91% at week 4. On the other hand, nighttime urgency in the group treated with Composition 2 decreased only 66% at week 4.

Figure 10:
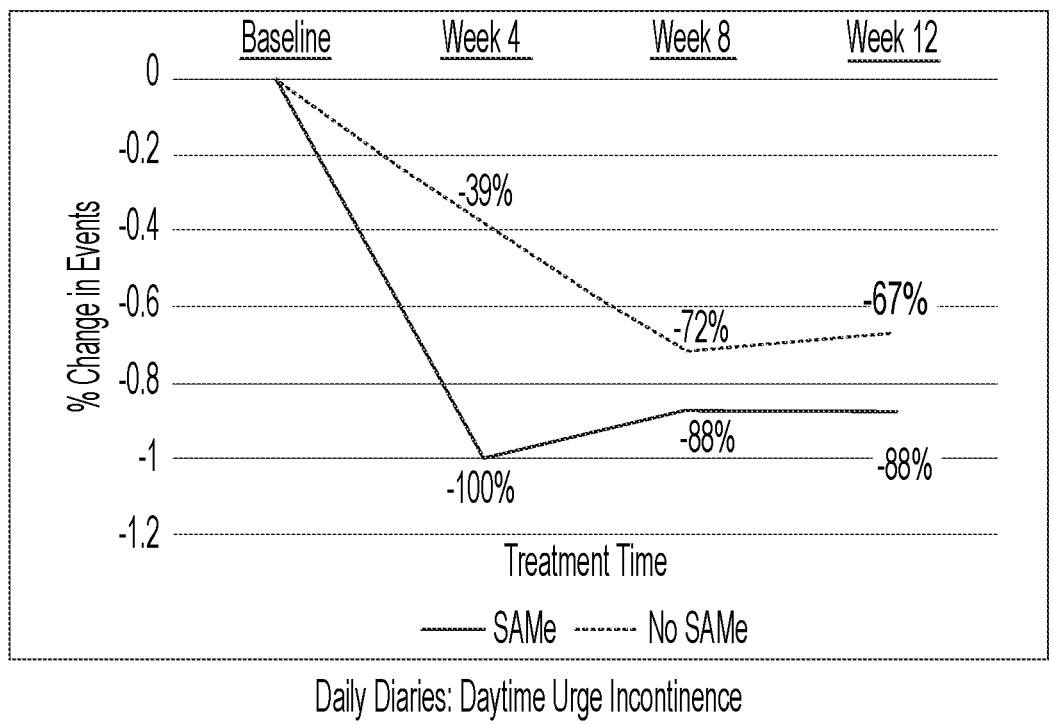
FIG. 10 shows daytime urge incontinence changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg yellow maca.

FIG. 10 shows that daytime urge incontinence in the group treated with Composition 1 decreased 100% at week 4, as compared to 39% of decrease in the group treated with Composition 2.

Figure 11:
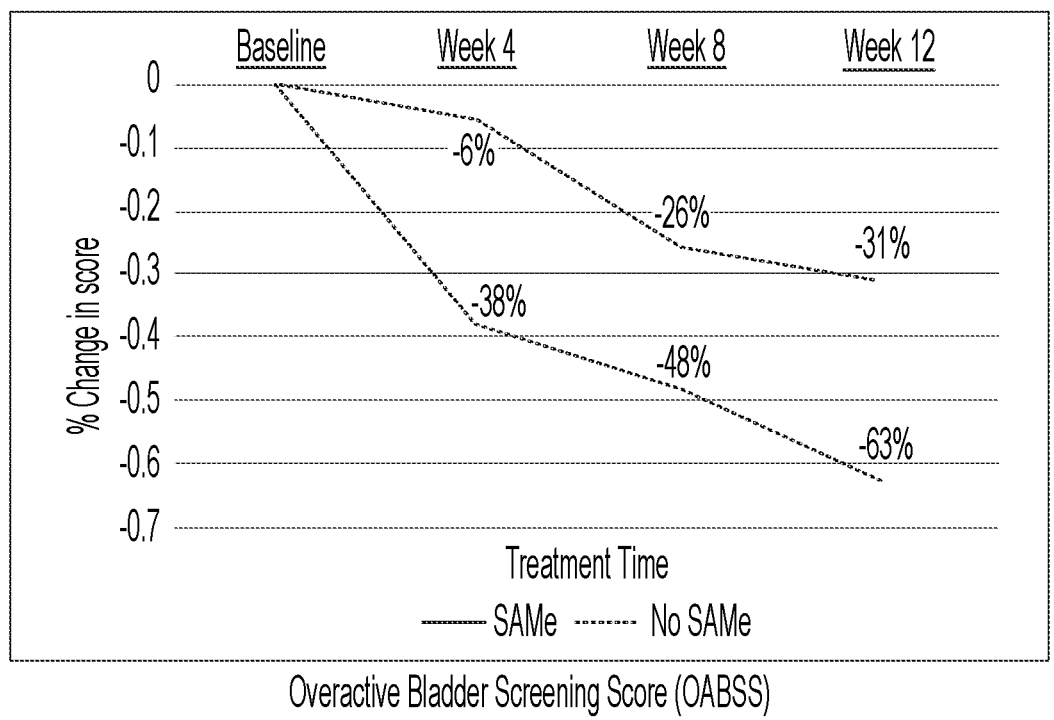
FIG. 11 shows overactive bladder screening score (OABSS) changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 11 shows that OABS scores in the group treated with Composition 1 decreased 38%, 48%, and 63% respectively at weeks 4, 8, and 12 and by contrast, OABS scores in the group treated with Composition 2 decreased 6%, 26%, and 31% respectively at weeks 4, 8, and 12.

Figure 12:
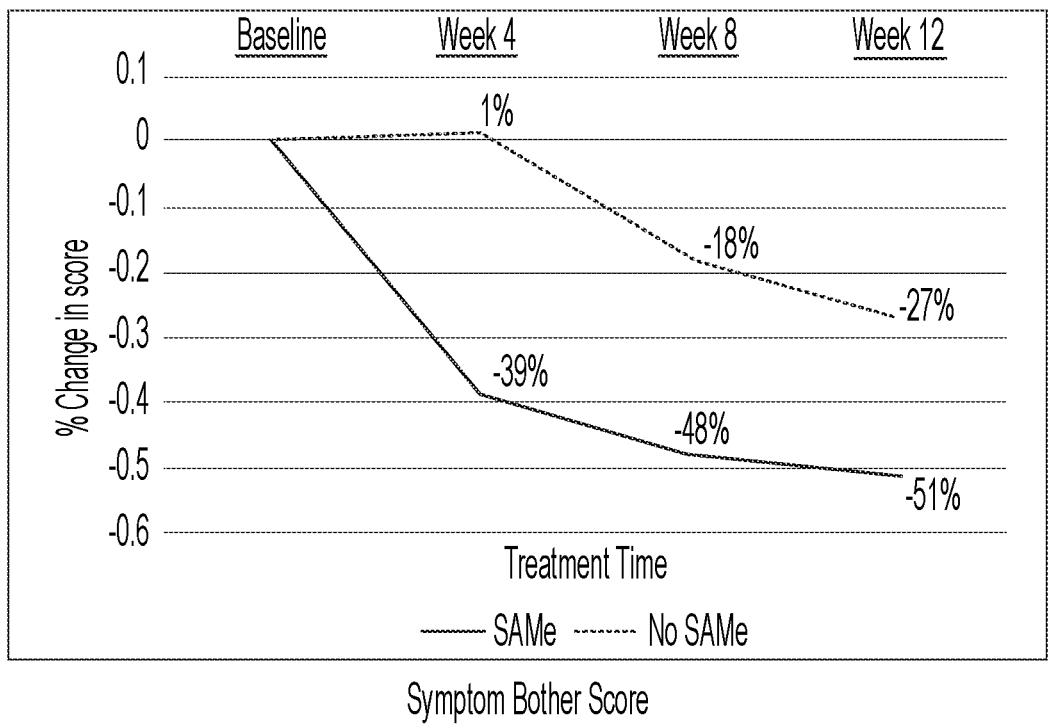
FIG. 12 shows symptom bother score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 12 shows that symptom bother scores in the group treated with Composition 1 decreased 39%, 48%, and 51% respectively at weeks 4, 8, and 12, while those in the group treated with Composition 2 increased 1% at week 4 and decreased 18% and 27% respectively at weeks 8 and 12.

Figure 13:
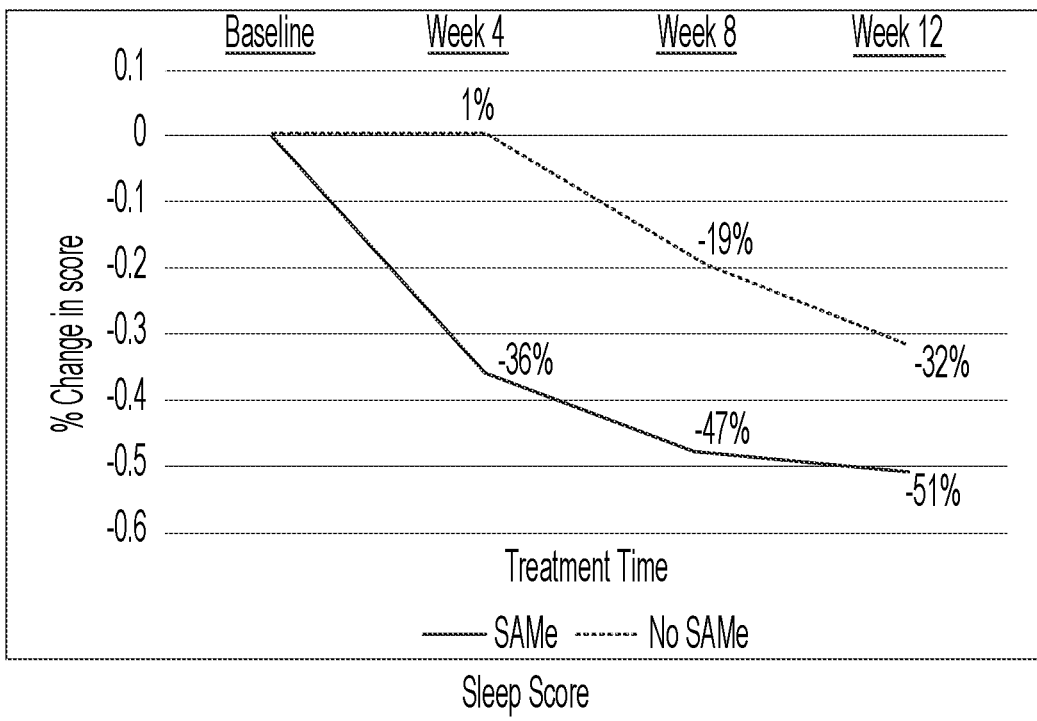
FIG. 13 shows sleep score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 13 shows that sleep scores in the group treated with Composition 1 decreased 36%, 47%, and 51% respectively at weeks 4, 8, and 12, while sleep scores in the group treated with Composition 2 increased 1% at week 4 and decreased 19% and 32% respectively at weeks 8 and 12.

Figure 14:
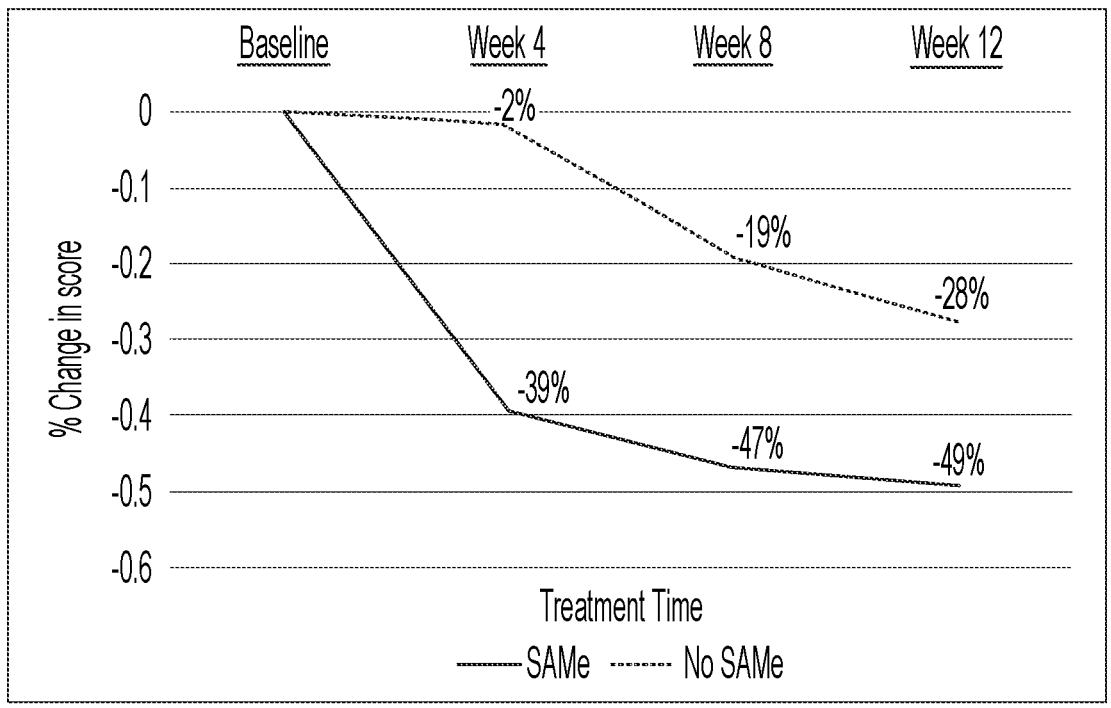
FIG. 14 shows health-related quality of life (HRQL) score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 14 shows that HRQL scores in the group treated with Composition 1 decreased 39%, 47%, and 49% respectively at weeks 4, 8, and 12, while HRQL scores in the group treated with Composition 2 decreased 2%, 19%, and 28% respectively at weeks 4, 8, and 12.

Figure 15:
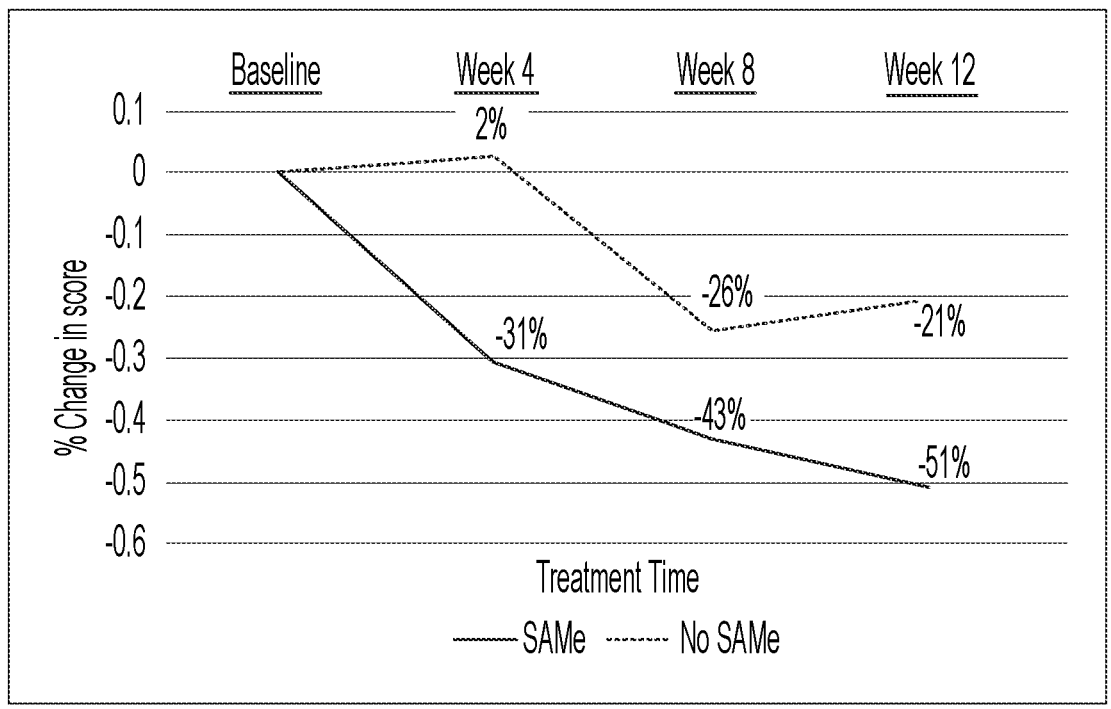
FIG. 15 shows daytime micturition score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 15 shows that daytime micturition scores in the group treated with Composition 1 decreased 31%, 43%, and 51% respectively at weeks 4, 8, and 12, while daytime micturition scores in the group treated with Composition 2 increased 2% at week 4 and decreased 26% and 21% respectively at weeks 8 and 12.

Figure 16:
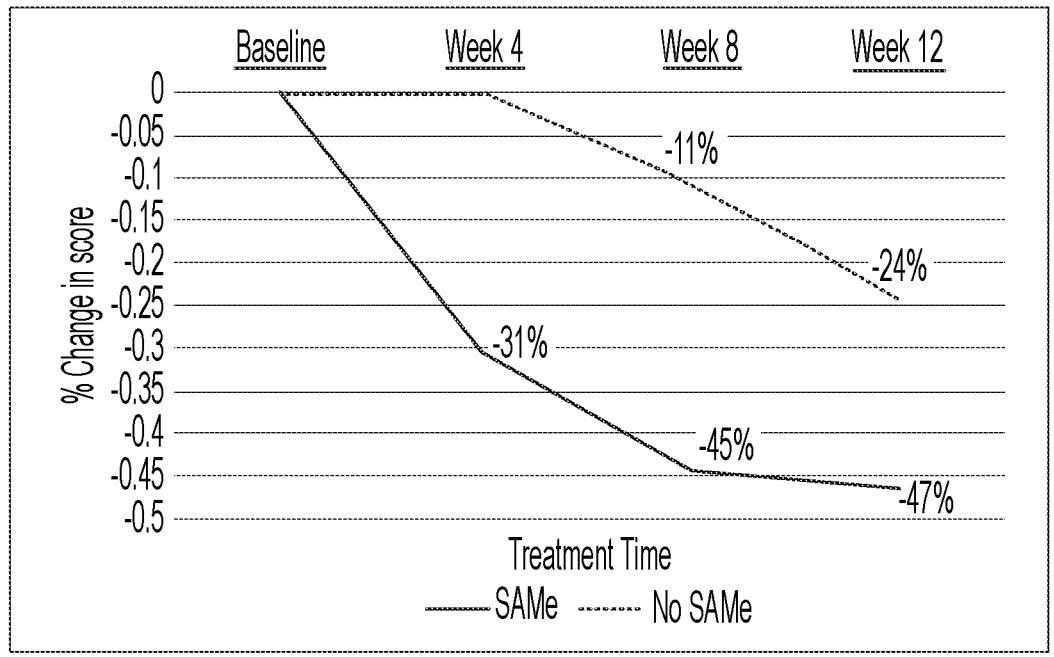
FIG. 16 shows nocturia score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 16 shows that nocturia scores in the group treated with Composition 1 decreased 31%, 45%, and 47% respectively at weeks 4, 8, and 12, while nocturia scores in the group treated with Composition 2 did not change during first 4 weeks of treatment and decreased 11% and 24% respectively at weeks 8 and 12.

Figure 17:
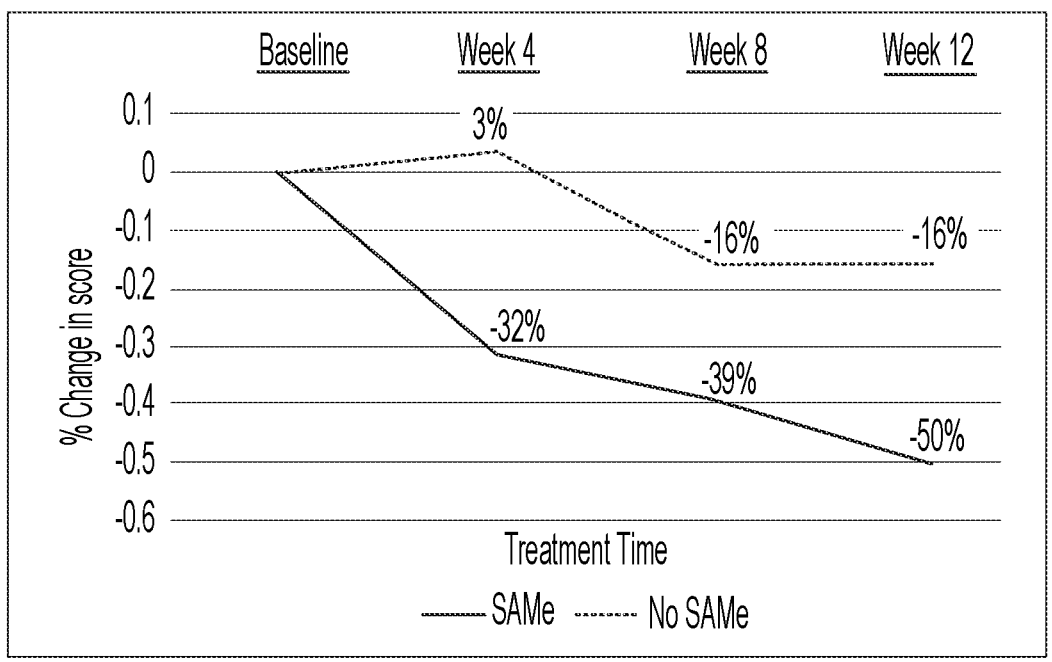
FIG. 17 shows urgency score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 17 shows that urgency scores in the group treated with Composition 1 decreased 32%, 39%, and 50% respectively at weeks 4, 8, and 12, while urgency scores in the group treated with Composition 2 increased 3% at week 4 and decreased 16% and 16% respectively at weeks 8 and 12.

Figure 18:
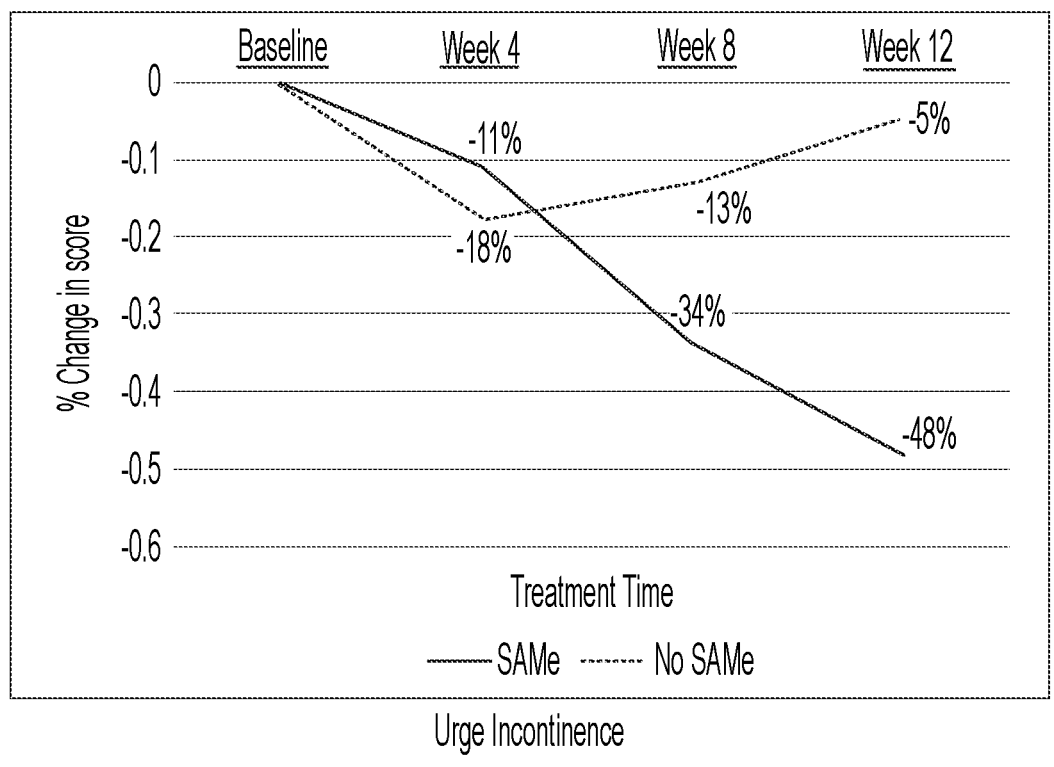
FIG. 18 shows urge incontinence score changes in a group treated with a composition comprising 200 mg of SAMe, 360 mg of *Crataeva nurvala*, and 250 mg of yellow maca and in a group treated with a composition comprising 360 mg of *Crataeva nurvala*, and 250 mg of yellow maca.

FIG. 18 shows that urge incontinence scores in the group treated with Composition 1 decreased 11%, 34%, and 48% respectively at weeks 4, 8, and 12, while urge incontinence scores in the group treated with Composition 2 decreased 18%, 13% and 5% respectively at weeks 4, 8, and 12.

FIGS. 6-18 all demonstrate that a composition described herein comprising a combination of a beta-adrenergic agonist and muscarinic antagonists is unexpectedly more effective than a composition comprising muscarinic antagonists but no beta-adrenergic agonist in treating and/or ameliorating overactive bladder symptoms, which is consistent with the results shown in Table 2.

TABLE 2

(OABS Scores)

| Average ± STDEV | Baseline | Week 4 | Week 8 | Week 12 |
|---|---|---|---|---|
| Composition 1 (SAMe) | 6.9 ± 2.0 | 4.2 ± 2.1 | 3.5 ± 1.5 | 2.5 ± 1.3 |
| Composition 2 (no-SAMe) | 6.2 ± 2.3 | 5.8 ± 2.2 | 4.6 ± 2.1 | 4.3 ± 2.3 |

Table 2 shows that, during the 12-week administration of Composition 1, participants experienced from moderate OAB symptoms to nearly no OAB symptoms and by contrast, during the 12-week administration of Composition 2, participants experienced from moderate OAB symptoms to mild OAB symptoms.

At the end of week 12, each participant administered Composition 1 conducted a consumer experience survey. The results are shown in Table 3 below.

TABLE 3

| Question | Feedback (Strongly Agree/ Agree) |
|---|---|
| I am satisfied with this product. | 68% |
| This product improved my overall quality of life. | 60% |
| This product helped me sleep through the night. | 58% |
| This product reduced the number of times I urinate due to my OAB condition. | 60% |
| I am more comfortable on a daily basis. | 68% |
| I have spent less time worrying about locating the bathroom while in public. | 57% |
| I am better able to focus and be more productive during the day. | 46% |
| Would you continue to use this product after the trial? | 76% |

Side effects of both compositions were also evaluated. Dry mouth and constipation were not observed in either group. Both Composition 1 and Composition 2 showed a lower incidence of side effects and adverse events than those frequently reported with pharmaceutical OAB compositions of the prior art.

Example 5

A randomized, double-blinded, placebo-controlled, and parallel clinical trial will be performed to determine the efficacy of a composition described herein in treating overactive bladder symptoms in women.

96 generally healthy women (ages of 40-65 years old) will participate in an online 3-day Home Bladder Monitoring Diary screening (adapted from the International Consultation on Incontinence Questionnaire bladder diary (Bright, Cotterill, Drake, & Abrams, 2014)) to determine if they have the following four lower urinary tract symptoms: (i) not less than eight times (day and night) micturitions per day, (ii) not less than twice nocturia per day, (iii) not less than three times urgency episodes per day, and (iv) less than 1 leakage episode per day. 80 women who experience all the four symptoms will be selected to participate in the trial.

The 80 participants will be randomly and equally divided into two groups, i.e., a placebo group and an active group. 24-48 hours before the trial, each participant will complete the following five online questionnaires:
(i) overactive bladder questionnaire (OAB-Q), including an eight-item symptom bother scale and a twenty-five-item health-related quality of life (HRQoL) scale. The HRQoL scale is divided into the three subscales: coping (eight items), concern (seven items), sleep (five items) and social interaction (five items). The HRQoL total score will be calculated by summating the individual HRQoL subscale scores;
(ii) OABS score;
(iii) patient perception of bladder condition (PPBC), measuring the participant's perception of their urinary (bladder) problems (Coyne, Matza, Kopp, & Abrams, 2006; Matza et al., 2005);
(iv) healthy days core module (HRQOL-4), used by the Centers for Disease Control and Prevention for various surveys including the National Health and Nutrition Examination Survey to assess health-related quality of life;
(v) sexual quality of life questionnaire-female (SQoL-F), an eighteen-item questionnaire specifically assessing the relationship between female sexual dysfunction and quality of life (Symonds, Boolell, & Quirk, 2005); and
(vi) PROMIS sleep disturbance short form 8B, assessing the pure domain of sleep disturbance (Yu et al., 2011).

During the trial, the placebo group will be orally administered with a placebo composition comprising sodium starch glycolate, magnesium stearate, microcrystalline cellulose, and triethyl citrate and the active group will be orally administered with an exemplary composition containing 360 mg of *Crataeva nurvala* dry bark powder, 45 mg of black maca dry powder, 45 mg of yellow maca dry powder, 150 mg of SAMe, 9 mg of propyl gallate, and the placebo composition. The compositions will be administered twice a day, once in the morning upon waking and the other before noon at least 30 minutes before a meal with 8 oz of water, for 84 consecutive days. Each participant will complete (a) 3-day Home Bladder Monitoring Diary on days 5-7, 12-14, 19-21, 26-28, 54-56, and 82-84, (b) online questionnaires (i)-(iv) and (vi) on days 28, 56, and 84, and (c) questionnaire (v) on day 84.

Changes from the baseline in the number of micturition and urge episodes without leakage/day (daytime and nighttime) will be calculated based on the data from (a) above. A micturition event is defined here as an occurrence whereby urine is expelled during the daytime and nighttime. An urge episode is defined here as an occurrence of urgency without leakage obtained from the Home Bladder Monitoring Diary. A day (daytime and night-time) is defined as the duration of time a subject wakes up in the morning to the time the participant wakes up in the morning the next day. The number of micturition and urge episodes collected at all collection periods during the intervention period (i.e., Days 5-7, Days 12-14, Days 19-21, Days 26-28, Days 54-56, and Days 82-84) will be summed and divided by 3 to obtain the number of micturitions/day (daytime and night-time) and urge episodes/day (daytime and night-time), respectively.

Further, changes from the baselines in the data obtained from (b) and (c) will also be determined.

OAB Product Experience Questionnaire will be conducted on day 84.

Adverse side effects such as dry mouth and constipation will be monitored.

While the present invention has been described in some detail for purposes of clarity and understanding, one will appreciate that various changes in form and detail can be made without departing from the true scope of the invention.

The invention claimed is:

1. A composition for supporting bladder health and/or treating overactive bladder or at least one symptom associated therewith comprising an amount of a beta-adrenergic receptor agonist and an amount of at least one muscarinic receptor antagonist, wherein the beta-adrenergic receptor agonist comprises S-adenosyl-L-methionine (SAMe) and wherein the at least one muscarinic receptor antagonist is the *Crataeva nurvala* plant material or extract thereof and a mixture of black maca and yellow maca, wherein the mixture of black maca and yellow maca comprises a ratio of black maca to yellow maca of about 4:1 to about 1:4.

2. The composition of claim 1, wherein the *Crataeva nurvala* plant material or extract thereof, the mixture of black maca and yellow maca, and the SAMe are present in a ratio of about 4:1:1 to about 4:1:4.

3. A composition for supporting bladder health and/or treating overactive bladder or at least one symptom associated therewith comprising an amount of a beta-adrenergic receptor agonist and an amount of at least one muscarinic receptor antagonist, wherein the beta-adrenergic receptor agonist comprises S-adenosyl-L-methionine (SAMe) and propyl gallate (PG), wherein SAMe and PG comprise a mixture having a ratio of SAMe to PG of about 8:1 to about 128:1, and wherein the at least one muscarinic receptor antagonist is selected from the group consisting of pumpkin seed, *Crataeva nurvala* plant material or an extract thereof, *Lindera aggregata* plant material or an extract thereof, black maca, yellow maca, phycocyanin or an extract thereof, and any combination thereof.

4. The composition of claim 3, wherein the at least one muscarinic receptor antagonist is the *Crataeva nurvala* plant material or extract thereof and a mixture of black maca and yellow maca, wherein the mixture of black maca and yellow maca comprises a ratio of black maca to yellow maca of about 4:1 to about 1:4.

5. The composition of claim 4, wherein the *Crataeva nurvala* plant material or extract thereof, the mixture of black maca and yellow maca, and the mixture of SAMe and PG are present in a ratio of about 4:1:1 to about 4:1:4.

6. The composition of claim 3, wherein the at least one muscarinic receptor antagonist is *Crataeva nurvala* plant material or extract thereof.

7. The composition of claim 3, wherein the at least one muscarinic receptor antagonist consists of pumpkin seed, *Crataeva nurvala* plant material or extract thereof, and *Lindera aggregata* plant material or extract thereof.

8. A dietary supplement comprising an amount of a beta-adrenergic receptor agonist and an amount of at least one muscarinic receptor antagonist, wherein the beta-adrenergic receptor agonist comprises S-adenosyl-L-methionine (SAMe) and wherein the at least one muscarinic receptor antagonist is *Crataeva nurvala* plant material or extract thereof and a mixture of black maca and yellow maca, wherein the mixture of black maca and yellow maca comprises a ratio of black maca to yellow maca of about 4:1 to about 1:4.

9. The dietary supplement of claim 8, wherein the *Crataeva nurvala* plant material or extract thereof, the mixture of black maca and yellow maca, and the SAMe are present in a ratio of about 4:1:1 to about 4:1:4.

10. The dietary supplement of claim 8, wherein the dietary supplement is administered to a subject, wherein the administration of the dietary supplement treats, ameliorates, prevents, or reduces overactive bladder or at least one symptom associated therewith, wherein the at least one symptom is selected from the group consisting of urinary urgency, urinary incontinence, urge incontinence, polyuria, nocturia, bladder spasms, and any combination thereof.

11. The dietary supplement of claim 8, wherein the dietary supplement is administered to maintain healthy levels of bladder activity and urinary frequency.

12. The dietary supplement of claim 8, wherein the dietary supplement is administered to maintain healthy levels of one or more of urinary urgency, urinary incontinence, urge incontinence, polyuria, nocturia, bladder spasms, and any combination thereof.

13. The dietary supplement of claim 8, wherein the dietary supplement is administered to support bladder health.

14. A dietary supplement comprising an amount of a beta-adrenergic receptor agonist and an amount of at least one muscarinic receptor antagonist, wherein the beta-adrenergic receptor agonist comprises S-adenosyl-L-methionine SAMe) and propyl gallate (PG), wherein SAMe and PG comprise a mixture having a ratio of SAMe to PG of about 8:1 to about 128:1, and wherein the at least one muscarinic receptor antagonist is selected from the group consisting of pumpkin seed, *Crataeva nurvala* plant material or an extract thereof, *Lindera aggregata* plant material or an extract thereof, black maca, yellow maca, phycocyanin or an extract thereof, and any combination thereof.

15. The dietary supplement of claim 14, wherein the at least one muscarinic receptor antagonist is *Crataeva nurvala* plant material or an extract thereof and a mixture of black maca and yellow maca, wherein the mixture of black maca and yellow maca comprises a ratio of black maca to yellow maca of about 4:1 to about 1:4.

16. The dietary supplement of claim 15, wherein the *Crataeva nurvala* plant material or an extract thereof, the mixture of black maca and yellow maca, and the mixture of SAMe and PG are present in a ratio of about 4:1:1 to about 4:1:4.

17. The dietary supplement of claim 14, wherein the at least one muscarinic receptor antagonist is *Crataeva nurvala* plant material or extract thereof.

18. The dietary supplement of claim 14, wherein the at least one muscarinic receptor antagonist consists of pumpkin seed, *Crataeva nurvala* plant material or extract thereof, and *Lindera aggregata* plant material or extract thereof.

19. The dietary supplement of claim 14, wherein the dietary supplement is administered to a subject, wherein the administration of the dietary supplement treats, ameliorates, prevents, or reduces overactive bladder or at least one symptom associated therewith, wherein the at least one symptom is selected from the group consisting of urinary urgency, urinary incontinence, urge incontinence, polyuria, nocturia, bladder spasms, and any combination thereof.

20. The dietary supplement of claim 14, wherein the dietary supplement is administered to maintain healthy levels of bladder activity and urinary frequency.

21. The dietary supplement of claim 14, wherein the dietary supplement is administered to maintain healthy levels of one or more of urinary urgency, urinary incontinence, urge incontinence, polyuria, nocturia, bladder spasms, and any combination thereof.

22. The dietary supplement of claim 14, wherein the dietary supplement is administered to support bladder health.

* * * * *